US010787523B2

(12) United States Patent
Rotello et al.

(10) Patent No.: US 10,787,523 B2
(45) Date of Patent: Sep. 29, 2020

(54) NANOPARTICLE-PROTEIN COMPLEX FOR INTRACELLULAR PROTEIN DELIVERY

(71) Applicant: University of Massachusetts, Boston, MA (US)

(72) Inventors: Vincent M. Rotello, Amherst, MA (US); Rubul Mout, Amherst, MA (US)

(73) Assignee: University of Massachusetts, Boston, MA (US)

( * ) Notice: Subject to any disclaimer, the term of this patent is extended or adjusted under 35 U.S.C. 154(b) by 359 days.

(21) Appl. No.: 15/547,404

(22) PCT Filed: Jan. 29, 2016

(86) PCT No.: PCT/US2016/015711
§ 371 (c)(1),
(2) Date: Jul. 28, 2017

(87) PCT Pub. No.: WO2016/123514
PCT Pub. Date: Aug. 4, 2016

(65) Prior Publication Data
US 2018/0022831 A1 Jan. 25, 2018

Related U.S. Application Data

(60) Provisional application No. 62/109,389, filed on Jan. 29, 2015, provisional application No. 62/132,798, filed on Mar. 13, 2015, provisional application No. 62/169,805, filed on Jun. 2, 2015.

(51) Int. Cl.
| | | |
|---|---|---|
| C07K 17/14 | (2006.01) | |
| A61K 47/69 | (2017.01) | |
| C12N 9/12 | (2006.01) | |
| C12N 9/22 | (2006.01) | |
| C12N 9/64 | (2006.01) | |
| C12N 9/96 | (2006.01) | |
| C12N 15/113 | (2010.01) | |
| C12N 15/90 | (2006.01) | |

(52) U.S. Cl.
CPC .......... *C07K 17/14* (2013.01); *A61K 47/6923* (2017.08); *C12N 9/1241* (2013.01); *C12N 9/22* (2013.01); *C12N 9/6467* (2013.01); *C12N 9/96* (2013.01); *C12N 15/113* (2013.01); *C12N 15/907* (2013.01); *C12Y 304/21078* (2013.01); *C12N 2310/20* (2017.05)

(58) Field of Classification Search
CPC ................ A61K 47/6923; C07K 17/14; C12Y 304/21078; C12N 15/113; C12N 15/907; C12N 2310/20; C12N 9/1241; C12N 9/22; C12N 9/6467; C12N 9/96
USPC ........ 435/455, 458, 463; 424/400, 450, 489, 424/499
See application file for complete search history.

(56) References Cited

U.S. PATENT DOCUMENTS

2009/0004118 A1  1/2009  Nie et al.

FOREIGN PATENT DOCUMENTS

| WO | WO-2012125182 A1 * | 9/2012 | ............... C12N 9/16 |
| WO | WO-2012125182 A1 | 9/2012 | |
| WO | WO-2015006290 A1 * | 1/2015 | ........... C12N 15/902 |
| WO | WO-2015006290 A1 | 1/2015 | |
| WO | WO-2016123514 A1 | 8/2016 | |

OTHER PUBLICATIONS

Tang et al. ACS Nano 2013, vol. 7, Issue 8, pp. 6667-6673. (Year: 2013).*
Jiang et al. Angew. Chem. Int. Ed. 54, (Nov. 12, 2014), 506-510. (Year: 2014).*
"International Application Serial No. PCT/US2016/015711, International Search Report dated Apr. 11, 2016", 2 pgs.
"International Application Serial No. PCT/US2016/015711, Written Opinion dated Apr. 11, 2016", 6 pgs.
Bönisch, C., et al., "Histone H2A variants in nucleosomes and chromatin: more or less stable", Nucleic Acids Res. 40, (2012), 10719-10741.
Chen, Baohui, et al., "Dynamic imaging of genomic loci in living human cells by an optimized CRISPR/Cas system", Cell 155, (2013), 1479-1491.
Chou, Leo Y., et al., "DNA assembly of nanoparticle superstructures for controlled biological delivery and elimination", Nature Nanotechnol. 9, (2014), 148-155.
Chung, Joo Eun, et al., "Self-assembled micellar nanocomplexes comprising green tea catechin derivatives and protein drugs for cancertherapy", Nature Nanotechnol. 9, (2014), 907-912.
Cox, D. B., et al., "Therapeutic genome editing: prospects and challenges", Nat. Med. 21, (2015), 121-131.
Cronican, J. J., et al., "Potent delivery of functional proteins into Mammalian cells in vitro and in vivo using a supercharged protein", ACS Chem. Biol. 5, (2010), 747-752.
Cronican, James J., "A Class of Human Proteins That Deliver Functional Proteins Into Mammalian Cells In Vitro and In Vivo", Chem, Biol., (2011), 10 pgs.
Dingwall, Colin, et al., "Protein Import Into the Cell Nucleus", Annu. Rev. Cell Biol. 2, (1986), 367-390.
Doudna, Jennifer A., et al., "The new frontier of genome engineering with CRISPR-Cas9", Science 346, (2014), 10 pgs.
Fletcher, Jordan M., "Self-assembling cages from coiled-coil peptide modules", Science 340, (2013), 595-599.
Glotzer, Sharon C., et al., "Anisotropy of building blocks and their assembly into complex structures", Nature Mater. 6, (2007), 557-562.

(Continued)

*Primary Examiner* — Janet L Epps-Smith
(74) *Attorney, Agent, or Firm* — Schwegman Lundberg & Woessner, P.A.

(57) ABSTRACT

Various embodiments disclosed relate to a nanoparticle-protein complex for intracellular protein delivery. In various embodiments, the present invention provides a nanoparticle-protein complex including a nanoparticle including an amine-containing ligand. The nanoparticle-protein complex also includes a protein comprising a carboxylic acid-containing tag.

19 Claims, 26 Drawing Sheets

(56) References Cited

OTHER PUBLICATIONS

González-Toro, D.C., "Concurrent binding and delivery of proteins and lipophilic small molecules using polymeric nanogels", J. Am. Chem. Soc. 134, (2012), 6964-6967.

Han, X., et al., "CRISPR-Cas9 delivery to hard-to-transfect cells via membrane deformation", Sci. Adv. 1, e1500454, (2015), 8 pgs.

Hsu, Patrick D., et al., "Development and applications of CRISPR-Cas9 for genome engineering", Cell 157, (2014), 1262-1278.

Hu, Minghui, et al., "Assembly of nanoparticle-protein binding complexes: from monomers to ordered arrays", Angew. Chem. Int. Ed. Engl. 119, (2007), 5203-5206.

Jiang, Wenzhi, et al., "Demonstration of CRISPR/Cas9/sgRNA-mediated targeted gene modification in *Arabidopsis*, tobacco, sorghumand rice", Nucleic Acids Res. 41, (2013), 12 pgs.

Jiang, Ying, et al., "Direct Cytosolic Delivery of siRNA Using Nanoparticle-Stabilized Nanocapsules", Angew. Chem. Int. Ed ., 54, (Nov. 12, 2014), 506-510.

Kiani, Samira, et al., "Cas9 gRNA engineering for genome editing, activation and repression", Nat. Methods 12, (2015), 6 pgs.

Kim, Sojung, et al., "Highly efficient RNA-guided genome editing in human cells via delivery of purified Cas9 ribonucleoproteins", Genome Res. 24, (2014), 26 pgs.

Kleinstiver, Benjamin P., et al., "Engineered CRISPR-Cas9 nucleases with altered PAM specificities", Nature 523, (2015), 17 pgs.

Lee, Hyukjin, et al., "Molecularly self-assembled nucleic acid nanoparticles for targeted in vivo siRNA delivery", Nature Nanotechnol. 7, (2012), 389-393.

Lieberman, Judy, "The ABCs of granule-mediated cytotoxicity: new weapons in the arsenal", Nature Rev. Immunol. 3, (2003), 361-370.

Liu, Jia, et al., "Efficient delivery of nuclease proteins for genome editing in human stem cells and primary cells", Nat. Protoc. 10, No. 11, (2015), 1842-1859.

Long, C., et al., "Prevention of muscular dystrophy in mice by CRISPR/Cas9-mediated editing of germline DNA", Science 345, (2014), 1184-1188.

Mout, R., et al., "Environmentally responsive histidine-carboxylate zipper formation between proteins and nanoparticles", Nanoscale 6, (2014), 8873-8877.

Nagy, Andras, "Cre recombinase: the universal reagent for genome tailoring", Genesis 26, (2000), 99-109.

Nie, Zhihing, et al., "Properties and emerging applications of self-assembled structures made from inorganic nanoparticles", Nature Nanotechnol. 5, (2010), 15-25.

Park, Jai, et al., "Terminal supraparticle assemblies from similarly charged protein molecules and nanoparticles", Nature Commun. 5, 3593, (2014), 9 pgs.

Ramakrishna, Suresh, et al., "Gene disruption by cell-penetrating peptide-mediated delivery of Cas9 protein and guide RNA", Genome Res. 24, (2014), 28 pgs.

Ran, F. A., et al., "Genome engineering using the CRISPR-Cas9 system", Nature Protoc. 8, (2013), 2281-2308.

Ran, F. A., et al., "n vivo genome editing using *Staphylococcus aureus* Cas9", Nature 520, (2015), 18 pgs.

Saha, K., "Surface functionality of nanoparticles determines cellular uptake mechanisms in mammalian cells", Small 9, (2013), 300-305.

Sander, Jeffry D., et al., "CRISPR-Cas systems for editing, regulating and targeting genomes", Nature Biotechnol. 32, (2014), 347-355.

Schumann, Kathrin, et al., "Generation of knock-in primary human T cells using Cas9 ribonucleoproteins", Proc. Natl. Acad. Sci. U S A. 112, (2015), 10437-10442.

Schwank, Gerald, et al., "Functional repair of CFTR by CRISPR/Cas9 in intestinal stem cell organoids of cystic fibrosis patients", Cell Stem Cell 13, (2013), 653-658.

Slaymaker, Ian M., "Rationally engineered Cas9 nucleases with improved specificity", Science aad5227, (2015), 8 pgs.

Sun, W., et al., "Self-Assembled DNA Nanoclews for the Efficient Delivery of CRISPR-Cas9 for Genome Editing", Angew. Chem. Int. Ed. Engl. 54, (2015), 12029-12033.

Tang, R, et al., "Direct Delivery of Functional Proteins and Enzymes to the Cytosol Using Nanoparticle-Stablllzed Nanocapsules", ACS Nano 2013 vol. 7 Issue 8, [Online]. Retrieved from the Internet: <DOI: 10.1021/nn402753y>, 6667-6673.

Tsien, Roger Y, "The Green Fluorescent Protein", Annu. Rev. Biochem., 67, (1998), 509-544.

Wu, Yuxuan, et al., "Correction of a Genetic Disease in Mouse via Use of CRISPR-Cas9", Cell Stem Cell 13, (2013), 659-662.

Yan, Ming, et al., "A novel intracellular protein delivery platform based on single-protein nanocapsules", Nat Nanotechnol, 5, (2010), 48-53.

Yang, Xiao-Chao, et al., "Drug delivery using nanoparticle-stabilized nanocapsules", Angew. Chem. Int. Ed. Engl. 50, (2011), 477-481.

Yin, Hao, et al., "Genome editing with Cas9 in adult mice corrects a disease mutation and phenotype", Nature Biotechnol. 32, (2014), 551-554.

You, Chang-Cheng, et al., "Tunable inhibition and denaturation of alpha-chymotrypsin with amino acid-functionalized gold nanoparticles", J. Am. Chem. Soc. 127, (2005), 12873-12881.

Zangi, Lior, et al., "Modified mRNA directs the fate of heart progenitor cells and induces vascular regeneration after myocardial infarction", Nature Biotechnol. 31, (2013), 14 pgs.

Zuris, John A., et al., "Cationic lipid-mediated delivery of proteins enables efficient protein-based genome editing in vitro and in vivo", Nat. Biotechnol. 33, (2015), 73-80.

\* cited by examiner

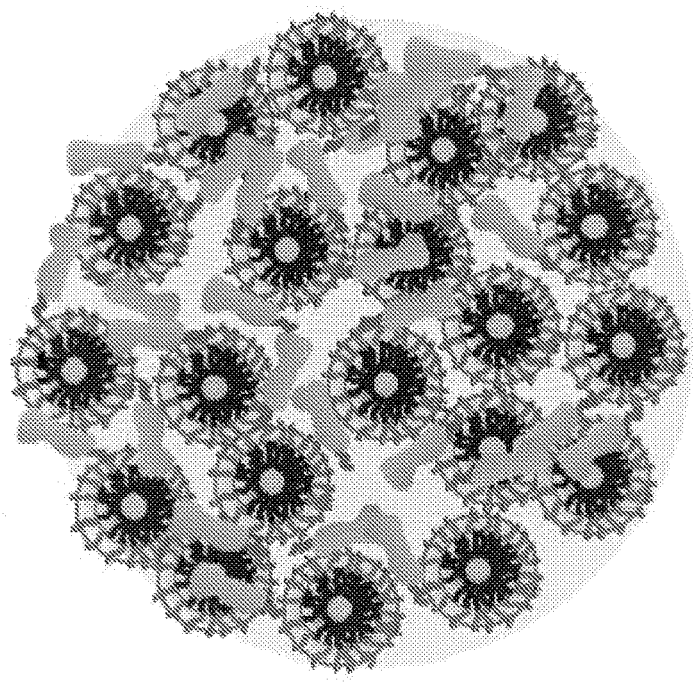
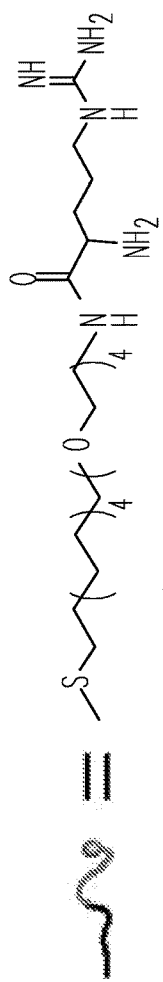
Fig. 1A

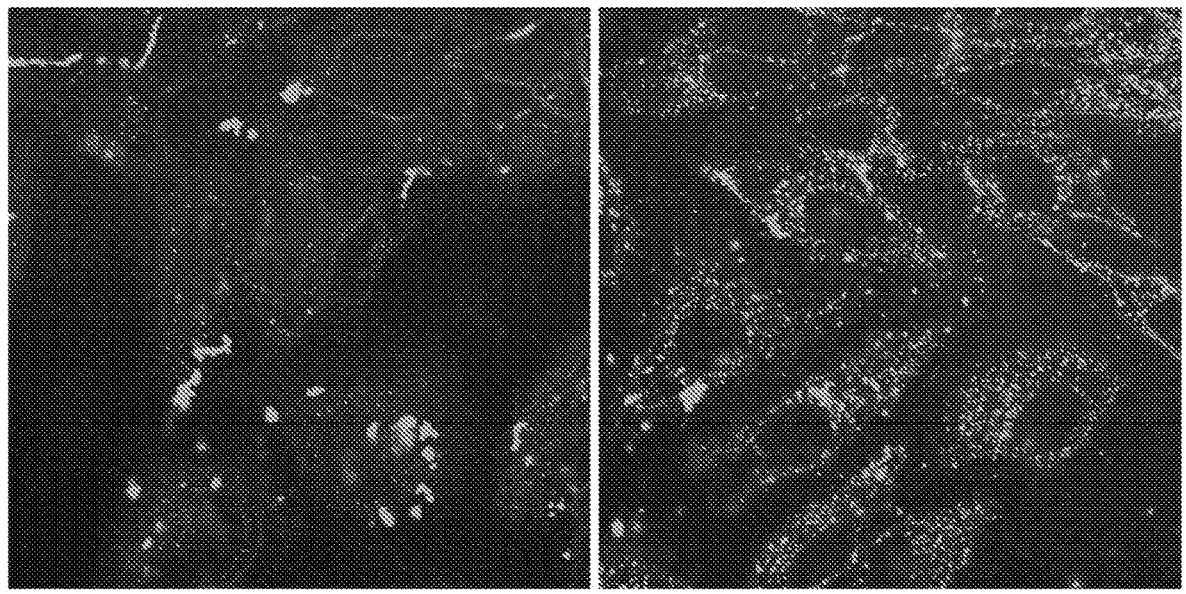
*Fig. 3A*  *Fig. 3B*
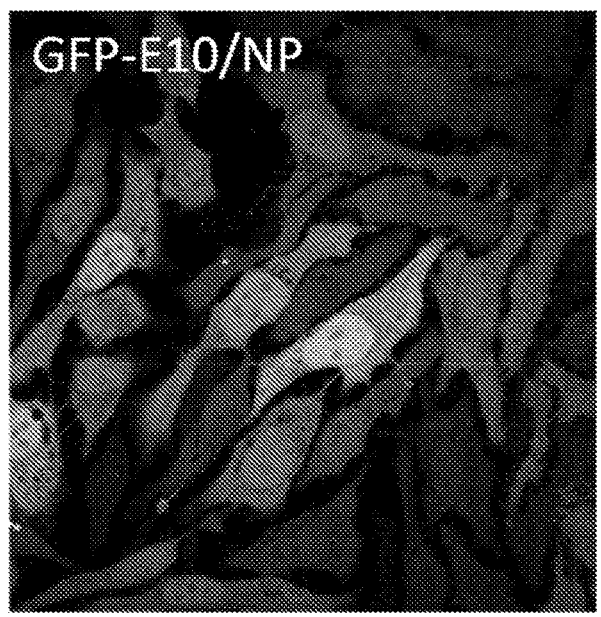
*Fig. 3C*

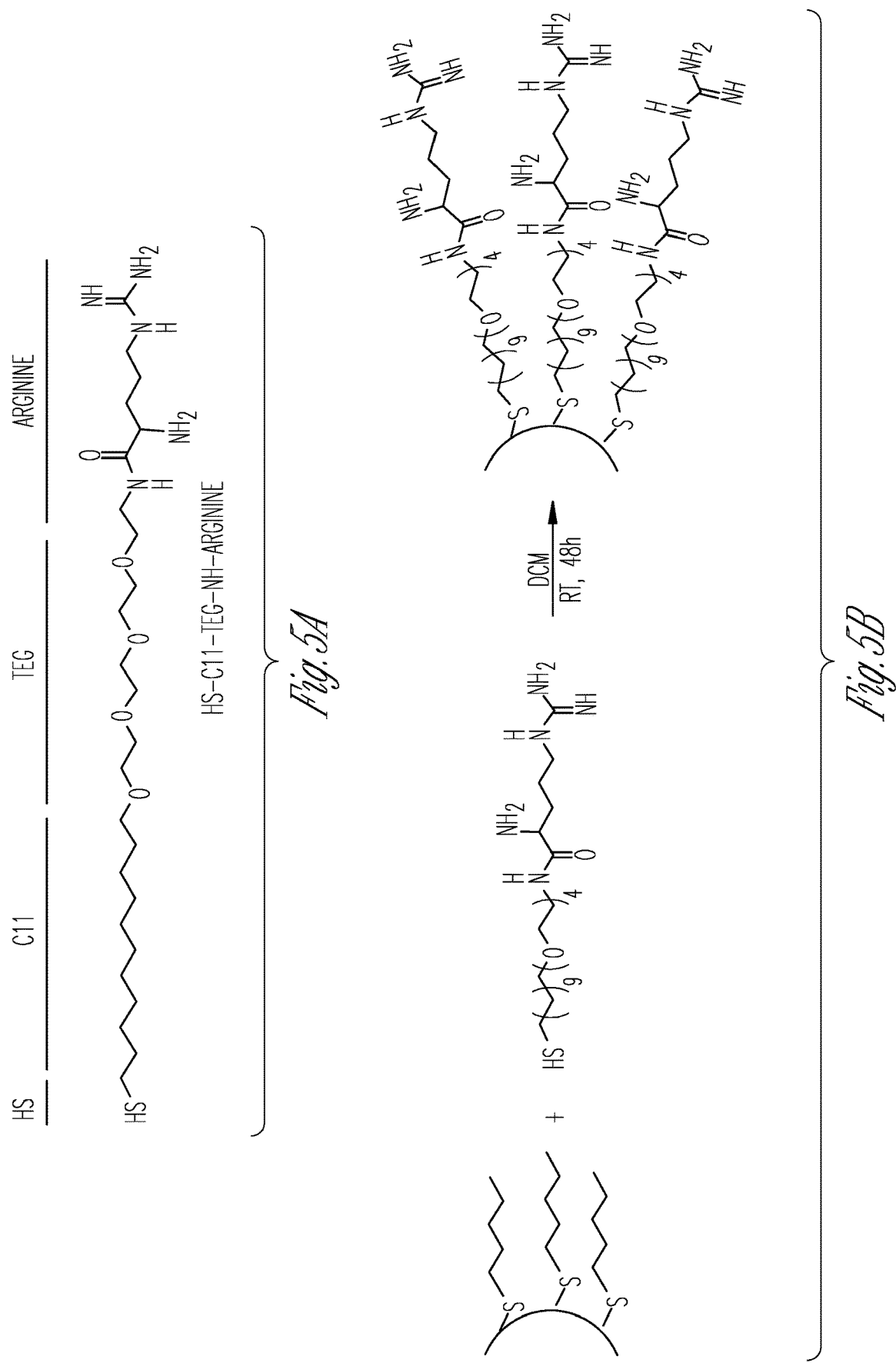

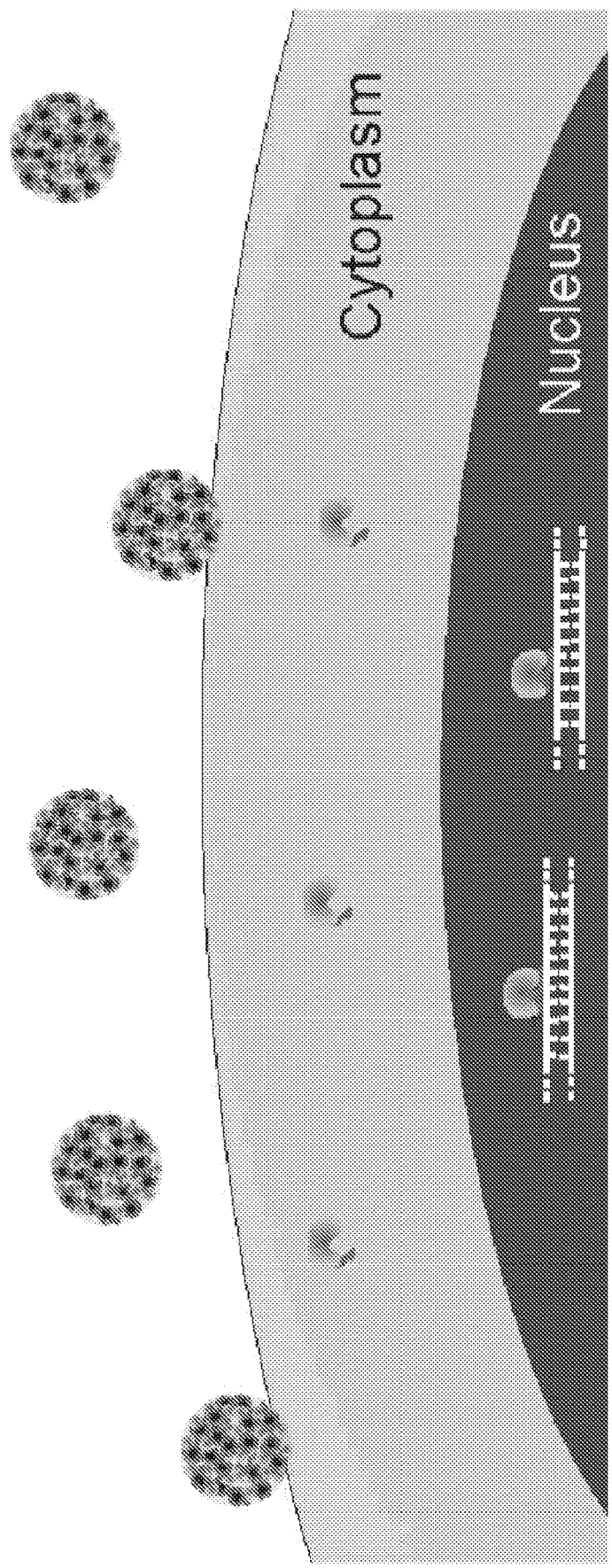

NANOPARTICLE-PROTEIN COMPLEX FOR INTRACELLULAR PROTEIN DELIVERY

PRIORITY APPLICATION

This application is a U.S. National Stage Filing under 35 U.S.C. 371 from International Application No. PCT/US2016/015711, filed on Jan. 29, 2016, and published as WO 2016/123514, which claims priority to U.S. Provisional Application Ser. No. 62/109,389, filed Jan. 29, 2015, U.S. Provisional Application Ser. No. 62/132,798, filed Mar. 13, 2015, and U.S. Provisional Application Ser. No. 62/169,805, filed Jun. 2, 2015, the disclosures of which are incorporated herein in their entirety by reference.

STATEMENT OF GOVERNMENT SUPPORT

This invention was made with Government support under EB014277-01 awarded by the National Institute of Health. The U.S. Government has certain rights in this invention.

BACKGROUND

Traditionally, to understand the function of a protein, it is customary to deliver a gene into a recipient cell, and subsequently observe the function of the protein encoded by the gene. Additionally, studying protein function is also important in variety of diseases including cancer. Certain intracellular proteins can't perform their functions in such diseased-cells. Therefore, replenishing the protein from outside is one of the ways of curing such diseases. This replenishment could be done either by directly delivering the protein, or via delivering the gene that makes the protein inside the cell. Despite the popularity of delivering a gene into a cell, it has many shortcomings. For example, the delivered gene permanently gets incorporated into the recipient cell's genome, causing long-term expression of the gene into a functional protein. Long-term expression of a protein may cause alteration in the cell physiology, and hence may not be desired. Further, the random incorporation of the gene into the recipient cell's genome frequently causes cancer.

An alternative to gene delivery is the direct delivery of a functional protein into cells. After the delivered protein gets into the cell, it can perform its function, and slowly be degraded away once its job' is completed. However, delivering a protein into a cell is quite challenging. Notably, due to its large size a protein can't freely diffuse through the cell membrane, requiring a 'delivery vehicle' for the transport across the membrane. Fabrication of a delivery vehicle for a protein depends on the physiochemical properties of the protein. However, the size and charge of protein vary from one to another, making it extremely challenging to fabricate a 'general' protein delivery platform. Therefore, most of the current delivery vehicles reported in literature can deliver only certain proteins into cells.

Another concerning aspect of protein delivery is that the delivered protein must reach its 'destination' compartment inside the cells. A cell has multiple compartments or organelles inside. A delivered protein may require access to these compartments for its function. Unfortunately, in case of majority of the protein delivery vehicles reported so far, delivered proteins get trapped in the endosomes that degrade the proteins and restricts their access to the destination organelles for their function.

SUMMARY OF THE INVENTION

In various embodiments, the present invention provides a nanoparticle-protein complex that includes a nanoparticle including an amine-containing ligand. The nanoparticle-protein complex also includes a protein including a carboxylic acid-containing tag.

In various embodiments, the present invention provides a nanoparticle-protein complex including a gold nanoparticle including an amine-containing ligand having the structure:

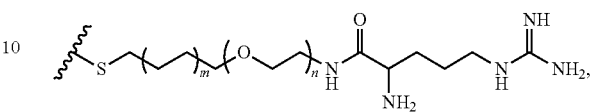

or a salt thereof. The variable m is 0 to 1,000 and n is 0 to 1,000. The nanoparticle-protein complex also includes a protein including a carboxylic acid-containing tag having the structure:

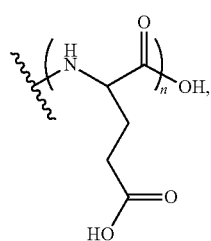

or a salt thereof, or,

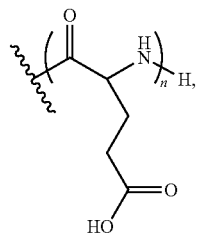

or a salt thereof.
The variable n is about 1 to about 10,000. The protein is chosen from GFP, Granzyme A, mCherry, Cre recombinase, Cas9, Histone 2A, and combinations thereof. The nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, and the nanoparticle-protein complex has about 1 to about 10,000 molecules of the protein. In various embodiments, the nanoparticle-protein complex includes a nucleic acid material that is gRNA (guide RNA). In various embodiments, nanoparticle-protein complex has about 1 to about 10,000 molecules of the nucleic acid material.

In various embodiments, the present invention provides a method of intracellular protein delivery. The method includes contacting a nanoparticle-protein complex with a cell. The nanoparticle-protein complex includes a nanoparticle including an amine-containing ligand. The nanoparticle-protein complex also includes a protein including a carboxylic acid-containing tag. The method also includes delivering the protein into the cell from the nanoparticle-protein complex.

In various embodiments, the present invention provides a method of intracellular protein and nucleic acid material delivery. The method includes contacting a nanoparticle-protein complex with a cell. The nanoparticle-protein complex includes a nanoparticle including an amine-containing ligand. The nanoparticle-protein complex includes a protein including a carboxylic acid-containing tag. The nanoparticle-protein complex also includes a nucleic acid material. The method includes delivering the protein and the nucleic acid material into the cell from the nanoparticle-protein complex.

In various embodiments, the present invention provides a method of intracellular protein delivery. The method includes contacting a nanoparticle-protein complex with a cell. The nanoparticle-protein complex includes a gold nanoparticle including an amine-containing ligand having the structure:

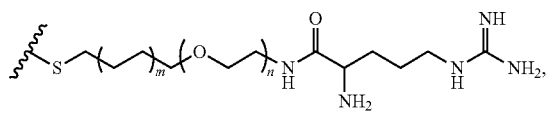

or a salt thereof. The variable m is 0 to 1,000 and n is 0 to 1,000. The nanoparticle-protein complex also includes a protein including a carboxylic acid-containing tag having the structure:

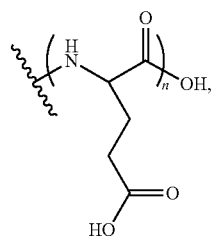

or a salt thereof,
or,

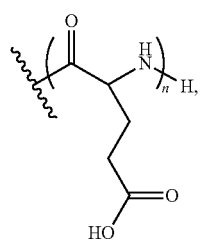

or a salt thereof.
The variable n is about 1 to about 10,000. The protein can be any suitable protein. The protein can be an antibody, an enzyme, a therapeutic protein, an imaging protein, or a combination thereof. The protein can be chosen from GFP, Granzyme A, mCherry, Cre recombinase, Cas9, Histone 2A, and combinations thereof. The nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, and the nanoparticle-protein complex has about 1 to about 10,000 molecules of the protein. The method also includes delivering the protein into the cell from the nanoparticle-protein complex. In some embodiments, the method is a method of intracellular protein and nucleic acid material delivery, wherein the nanoparticle-protein complex has about 1 to about 10,000 molecules of a nucleic acid material that is gRNA. In some embodiments, the method includes delivering the protein and the nucleic acid material into the cell from the nanoparticle-protein complex.

In various embodiments, the present invention provides a method of forming a nanoparticle-protein complex. The method includes combining a nanoparticle including an amine-containing ligand with a protein including a carboxylic acid-containing tag to form a self-assembled nanoparticle-protein complex.

In various embodiments, the present invention provides a method of forming a nanoparticle-protein complex. The method includes combining a nanoparticle including an amine-containing ligand with a protein including a carboxylic acid-containing tag and a nucleic acid material to form a self-assembled nanoparticle-protein complex that includes the nucleic acid material.

In various embodiments, the present invention provides a method of forming a nanoparticle-protein complex. The method includes combining a gold nanoparticle including an amine-containing ligand having the structure:

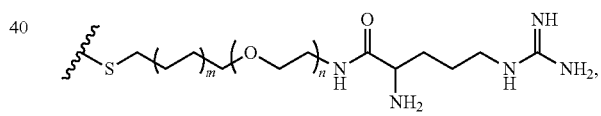

or a salt thereof, wherein m is 0 to 1,000 and n is 0 to 1,000, wherein the gold nanoparticle has a largest dimension of about 1 nm to about 50 nm and the gold nanoparticle has about 1 to about 10,000 of the amine-containing ligands, with
a protein including a carboxylic acid-containing tag having the structure:

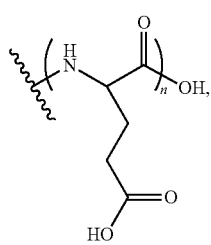

or a salt thereof,
or,

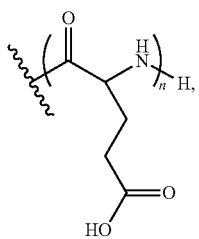

or a salt thereof,
wherein n is about 1 to about 10,000, wherein the protein is chosen from GFP, Granzyme A, mCherry, Cre recombinase, Cas9, Histone 2A, and combinations thereof, wherein in solution the protein has a largest dimension of about 0.5 nm to about 50 nm. The combining forms a self-assembled nanoparticle-protein complex. The nanoparticle-protein complex has a largest dimension of about 50 to about 999 nm, the nanoparticle-protein complex has about 1 to about 10,000 of the gold nanoparticles, and the nanoparticle-protein complex has about 1 to about 10,000 molecules of the protein.

In various embodiments, the present invention provides a method of forming a nanoparticle-protein complex. The method includes combining a gold nanoparticle including an amine-containing ligand having the structure:

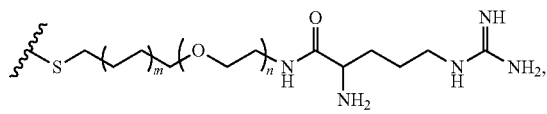

or a salt thereof, wherein m is 0 to 1,000 and n is 0 to 1,000, wherein the gold nanoparticle has a largest dimension of about 1 nm to about 50 nm and the gold nanoparticle has about 1 to about 10,000 of the amine-containing ligands, with a complex including
  a protein including a carboxylic acid-containing tag having the structure:

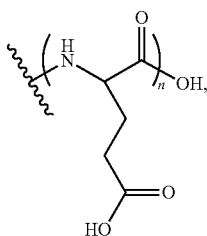

or a salt thereof,
or,

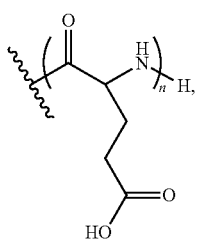

or a salt thereof.

wherein n is about 1 to about 10,000, wherein the protein is chosen from GFP, Granzyme A, mCherry, Cre recombinase, Cas9, Histone 2A, and combinations thereof, wherein in solution the protein has a largest dimension of about 0.5 nm to about 50 nm. The complex also includes a nucleic acid material that is gRNA. The combining of the gold nanoparticle and the complex including the protein and the nucleic acid material forms a self-assembled nanoparticle-protein complex that includes the nucleic acid material, wherein the nanoparticle-protein complex has a largest dimension of about 50 to about 999 nm, the nanoparticle-protein complex has about 1 to about 10,000 of the gold nanoparticles, the nanoparticle-protein complex has about 1 to about 10,000 molecules of the protein, and the nanoparticle-protein complex has about 1 to about 10,000 molecules of the gRNA.

Various embodiments of the present invention provide certain advantages over other complexes for intracellular protein delivery and methods of using the same. For example, other techniques for intracellular protein delivery are restricted to only certain types of proteins. In various embodiments, the present invention provides a more versatile delivery strategy. In various embodiments, the nanoparticle-protein complex can delivery any protein of interest to a cell. Other techniques for intracellular protein delivery can only deliver to undesired organelles within cells, or deliver a portion of the proteins to undesired organelles. In various embodiments, the nanoparticle-protein complex can deliver some or all of the protein to the cytoplasm within the cell, or to a desired organelle. In various embodiments, the nanoparticle-protein complex can provide a more efficient and straightforward method for delivering proteins to cells. In various embodiments, the nanoparticle-protein complex can be used for in vitro applications and in vivo therapeutic strategies.

In various embodiments, the nanoparticle-protein complex can include a nucleic acid material and can be used to deliver the nucleic acid material to cells along with the protein. In various embodiments, simultaneous delivery of both the protein and the nucleic acid material provides a convenient and practical method of genome editing (e.g., to cure genetic diseases), such as via CRISPR (clustered regularly interspaced short palindromic repeat).

BRIEF DESCRIPTION OF THE FIGURES

The drawings illustrate generally, by way of example, but not by way of limitation, various embodiments discussed in the present document.

FIG. 1A is a scheme showing fabrication of NP-protein assemblies, in accordance with various embodiments.

FIG. 3A illustrates a photomicrograph of GFP delivered via cell penetrating peptides (CPP).

FIG. 3B illustrates a photomicrograph of GFP delivered via +36-GFP.

FIG. 3C illustrates a photomicrograph of GFP delivered via E-10/NP, in accordance with various embodiments.

FIG. 5A illustrates the chemical structure of HS-C11-TEG-NH-Arginine ligand, in accordance with various embodiments.

FIG. 5B illustrates a scheme showing place-exchange for the preparation of ArgNPs, in accordance with various embodiments.

FIG. 6B illustrates a scheme showing delivery of E-tagged Cas9 into cells using arginine functionalized gold nanoparticles with E-tagged Cas9, in accordance with various embodiments.

DETAILED DESCRIPTION OF THE INVENTION

Figure 1B:
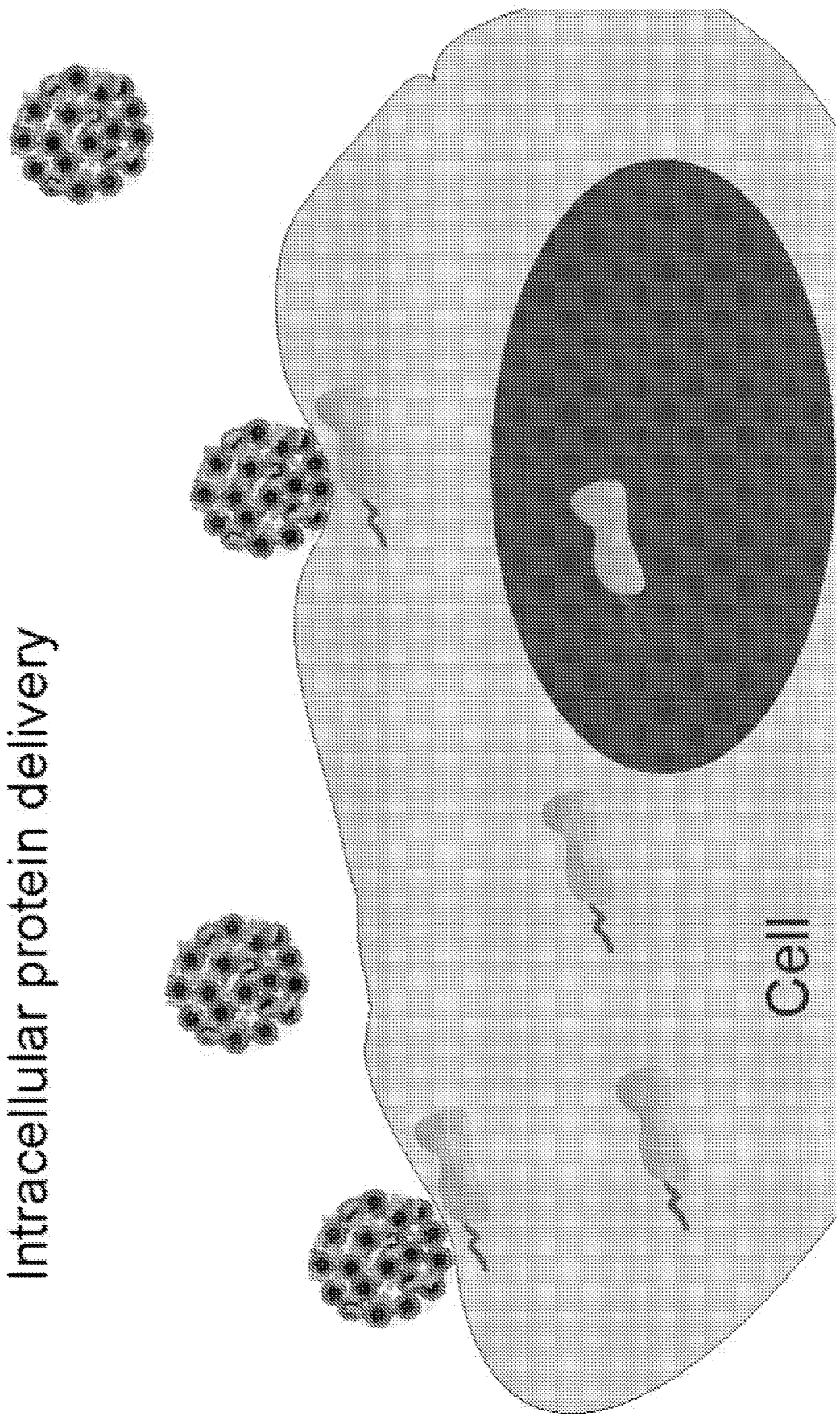
FIG. 1B is a scheme showing use of NP-protein assemblies for intracellular protein delivery, in accordance with various embodiments.
Figure 2F:
FIG. 2A-2F illustrates intracellular delivery of various engineered 'E10-tagged' proteins into HeLa cells, in accordance with various embodiments.
Figure 2C:
Figure 2E:
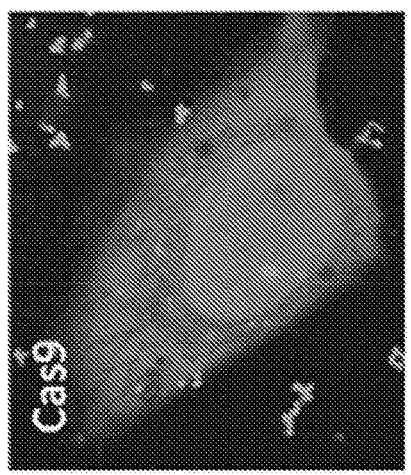
Figure 2B:
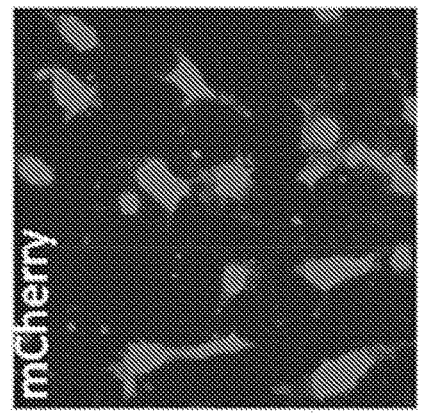
Figure 2D:
Figure 2A:

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, within 1%, or within 0% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species i having $n_i$ molecules of molecular weight $M_i$ through the formula $M_n = \Sigma M_i N_i / \Sigma n_i$. The number-average molecular weight can be measured by a variety of well-known methods including gel permeation chromatography, spectroscopic end group analysis, and osmometry. If unspecified, molecular weights of polymers given herein are number-average molecular weights.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof.

The term "solvent" as used herein refers to a liquid that can dissolve a solid, liquid, or gas. Nonlimiting examples of solvents are silicones, organic compounds, water, alcohols, ionic liquids, and supercritical fluids.

Salts herein that include a positive counterion (e.g., carboxylic acid salts) can include any suitable positive counterion. For example, the counterion can be ammonium ($NH_4^+$), or an alkali metal such as sodium (Na+), potassium ($K^+$), or lithium ($Li^+$). In some embodiments, the counterion can have a positive charge greater than +1, which can in some embodiments complex to multiple ionized groups, such as $Zn^{2+}$, $Al^{3+}$, or alkaline earth metals such as $Ca^{2+}$ or $Mg^{2+}$. $Na^+$, $K^+$, $Li^+$, $Zn^+$, $NH_4^+$, $Fe^{2+}$, $Fe^{3+}$, $Cu^{1+}$, $Cu^{2+}$, $Ca^{2+}$, $Mg^{2+}$, $Zn^{2+}$, and an $Al^{3+}$.

Salts herein that include a negative counterion (e.g., ammonium salts) can include any suitable negative counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

Nanoparticle-Protein Complex.

In various embodiments, the present invention provides a nanoparticle-protein complex. The nanoparticle-protein complex includes a nanoparticle including an amine-containing ligand. The nanoparticle-protein complex also includes a protein including a carboxylic acid-containing tag. In some embodiments, the nanoparticle-protein complex also includes a nucleic acid. The nanoparticle, the protein, and the nucleic acid (if present) can be complexed together via electrostatic interactions, such as via electrostatic interactions of the amine-containing ligand with the carboxylic acid-containing tag. The amine-containing ligand and the carboxylic acid-containing tag can be designed such that virtually any protein can be included in the nanoparticle-protein complex. Likewise, the amine-containing ligand and the protein can be chosen such that a desired nucleic acid material can be included in the nanoparticle-protein complex. In some embodiments, the nanoparticle-protein complex can be used to deliver the protein (and the nucleic acid, if present) to the interior of a cell, such as in vitro or in vivo.

The nanoparticle-protein complex can have any suitable size. In some embodiments, the nanoparticle-protein complex can have a largest dimension of about 50 nm to about 999 nm, about 150 nm to about 250 nm, or about 50 nm or less, or about 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 380, 400, 450, 500, 600, 700, 800, 900, or about 999 nm or more.

In some embodiments, the nanoparticle-protein complex can further include an antibody, such as an antibody containing a carboxylic acid-containing tag, such as any carboxylic acid-containing tag described herein. In some embodiments, specific cells can be targeted by the nanoparticle-protein complex by using an antibody. An antibody that specifically binds to cell surface markers is useful in this case. An antibody can be engineered with a carboxylic acid-containing tag, such as any carboxylic acid-containing tag described herein. The antibody with the tag can be assembled together with the both an S-tagged antibody and an E-tagged desired protein can be assembled together with the nanoparticle including an amine-containing ligand and the protein including a carboxylic acid-containing tag to form the nanoparticle-protein complex. The antibody can direct the assembly to a specific cell population based on the surface marker, while delivering the desired protein into the cell.

Nanoparticle Including an Amine-Containing Ligand.

The nanoparticle-protein complex includes a nanoparticle including an amine-containing ligand. The nanoparticle-protein complex can include one nanoparticle including an amine-containing ligand, or more than one nanoparticle including an amine-containing ligand. In some embodiments, the nanoparticle-protein complex includes about 1 to about 10,000 nanoparticles including an amine-containing ligand, or about 1 to about 1,000, about 50 to about 150, or about 1, 2, 3, 4, 5, 6, 7, 8, 9, 10, 12, 14, 16, 18, 20, 22, 24, 26, 28, 30, 35, 40, 45, 50, 60, 70, 80, 90, 100, 125, 150, 175, 200, 225, 250, 300, 400, 500, 600, 700, 800, 900, 1,000, 1,250, 1,500, 1,750, 2,000, 2,250, 2,500, 3,000, 4,000, 6,000, 8,000, or about 10,000 or more.

The nanoparticle including the amine-containing ligand can be any suitable nanoparticle, such as a gold nanoparticle, an iron oxide nanoparticle, a cobalt ferrite nanoparticle, a silica nanoparticle, a nanoparticle that includes any combination of the same, or a quantum dot (e.g. a cadmium selenide or zinc sulfide quantum dot). A gold nanoparticle including the amine-containing ligand can be any suitable gold nanoparticle. The nanoparticle-protein complex can include one type of nanoparticle including an amine-containing ligand, or multiple types of nanoparticles. The nanoparticle including the amine-containing ligand can have any suitable size. For example, the nanoparticle including the amine-containing ligand can have a largest dimension of 1 nm to about 50 nm, about 5 nm to about 15 nm, or about 1 nm or less, or about 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, or about 50 nm or more.

The nanoparticle can include one type of amine-containing ligand or more than one type of amine-containing ligand. The nanoparticle can include any suitable number of the amine-containing ligands. For example, the nanoparticle including the amine-containing ligand can include about 1 to about 10,000 of the amine-containing ligands, about 1 to about 1,000, about 50 to about 150, or about 1, 2, 3, 4, 5, 6, 7, 8, 9, 10, 12, 14, 16, 18, 20, 22, 24, 26, 28, 30, 35, 40, 45, 50, 60, 70, 80, 90, 100, 125, 150, 175, 200, 225, 250, 300, 400, 500, 600, 700, 800, 900, 1,000, 1,250, 1,500, 1,750, 2,000, 2,250, 2,500, 3,000, 4,000, 6,000, 8,000, or about 10,000 or more.

The amine-containing ligand can be any suitable amine-containing ligand that allows for self-assembly of the protein with the carboxylic acid-containing tag with the nanoparticle including the amine-containing ligand; e.g., the carboxylic acid-containing tag is electrostatically compatible with the amine-containing ligand of the nanoparticle. The amine-containing ligand can be a guanidine-containing ligand, such as a guanidine-terminated ligand. The amine-containing ligand can be an arginine-containing ligand, such as an arginine-terminated ligand.

In various embodiments, the amine-containing ligand is terminated with an amine-substituted or amine-containing $(C_0-C_{20})$hydrocarbyl group that is otherwise substituted or unsubstituted. The amine-substituted or amine-containing $(C_0-C_{20})$hydrocarbyl group can be tethered to the nanoparticle via a bond or via a linker that includes at least one of a) a substituted or unsubstituted $(C_1-C_{30})$hydrocarbylene interrupted or terminated with 0, 1, 2, or 3 groups independently chosen from —O—, —S—, and substituted or unsubstituted —NH—, and b) a poly(substituted or unsubstituted $(C_2-C_{10})$hydrocarbyloxy). The amine-substituted or amine-containing $(C_0-C_{20})$hydrocarbyl group can be tethered to the nanoparticle via a bond or via a linker that includes at least one of a $(C_1-C_{20})$alkylene and a poly($(C_2-C_3)$alkoxy), wherein the linker is bound to the nanoparticle via an —S—.

In various embodiments, the amine-containing ligand has the structure:

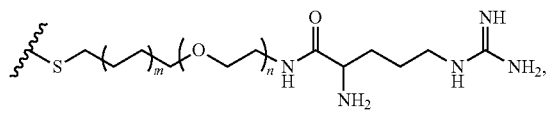

or a salt thereof, wherein m is 0 to 1,000 (e.g., 0, 1, 2, 3, 4, 5, 6, 7, 8, 9, 10, 12, 14, 16, 18, 20, 22, 24, 26, 28, 30, 35, 40, 45, 50, 60, 70, 80, 90, 100, 125, 150, 175, 200, 225, 250, 300, 400, 500, 600, 700, 800, 900, or about 1,000) and n is 0 to 1,000 (e.g., 0, 1, 2, 3, 4, 5, 6, 7, 8, 9, 10, 12, 14, 16, 18, 20, 22, 24, 26, 28, 30, 35, 40, 45, 50, 60, 70, 80, 90, 100, 125, 150, 175, 200, 225, 250, 300, 400, 500, 600, 700, 800, 900, or about 1,000).

In various embodiments, the amine-containing ligand has the structure:

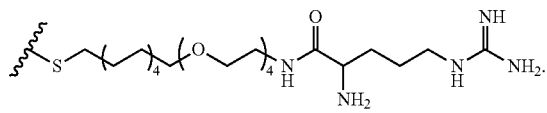

Protein Including a Carboxylic Acid-Containing Tag.

The nanoparticle-protein complex includes a protein including a carboxylic acid-containing tag. The nanoparticle-protein complex can include one protein including a carboxylic acid-containing tag, or more than one protein including a carboxylic acid-containing tag. In some embodiments, the nanoparticle-protein complex includes about 1 to about 10,000 molecules of the protein including the carboxylic acid-containing tag, or about 1 to about 1,000, about 50 to about 150, or about 1, 2, 3, 4, 5, 6, 7, 8, 9, 10, 12, 14, 16, 18, 20, 22, 24, 26, 28, 30, 35, 40, 45, 50, 60, 70, 80, 90, 100, 125, 150, 175, 200, 225, 250, 300, 400, 500, 600, 700, 800, 900, 1,000, 1,250, 1,500, 1,750, 2,000, 2,250, 2,500, 3,000, 4,000, 6,000, 8,000, or about 10,000 or more.

The protein in the nanoparticle-protein complex can be any suitable protein.

The nanoparticle-protein complex can include one type of protein, or multiple types of proteins. In some examples, the protein is chosen from GFP, Granzyme A, mCherry, Cre recombinase, Cas9, Histone 2A, and combinations thereof. The protein including the carboxylic acid-containing tag can have any suitable size. For example, the protein including the carboxylic acid-containing tag can have a largest dimension of about 0.5 nm to about 50 nm, about 1 nm to about 30 nm, or about 0.5 nm or less, or about 1 nm, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, or about 50 nm or more.

The protein can include on carboxylic acid-containing tag or multiple carboxylic acid containing tags. The carboxylic acid-containing tag can be located at any suitable position on the protein. In some embodiments, the carboxylic acid-containing tag can be located at a terminal position on the protein. The carboxylic acid-containing tag can be located on at least one of a C-terminus and an N-terminus of the protein.

The carboxylic acid-containing tag can be any suitable tag that allows for self-assembly of the protein including the carboxylic acid-containing tag with the nanoparticle including the amine-containing ligand; e.g., the carboxylic acid-containing tag is electrostatically compatible with the amine-containing ligand of the nanoparticle. The carboxylic acid-containing tag can be a polycarboxylic acid tag, e.g., a group including more than one carboxylic acid group. The carboxylic acid-containing tag can be a poly(amino acid) tag. The carboxylic acid-containing tag can be a glutamic acid-containing tag, such as a poly(glutamic acid) tag. In some embodiments, the carboxylic acid tag can include one or more of the following repeating units:

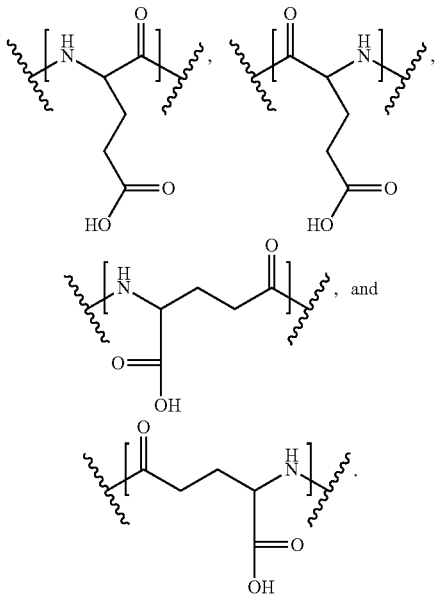

In various embodiments, the carboxylic acid-containing tag can have the structure:

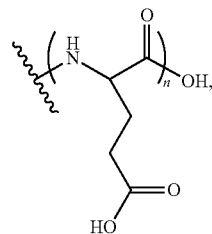

or a salt thereof, or,

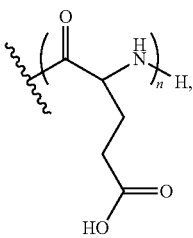

or a salt thereof.

The variable n can be about 1 to about 10,000, about 1 to about 1,000, about 5 to 20, about 10 to 15, or about 1, 2, 3, 4, 5, 6, 7, 8, 9, 10, 11, 12, 13, 14, 15, 16, 17, 18, 19, 20, 22, 24, 26, 28, 30, 35, 40, 45, 50, 60, 70, 80, 90, 100, 125, 150, 175, 200, 225, 250, 300, 400, 500, 600, 700, 800, 900, 1,000, 1,250, 1,500, 1,750, 2,000, 2,250, 2,500, 3,000, 4,000, 6,000, 8,000, or about 10,000 or more.

In various embodiments, the protein can include an organelle localization signal at any suitable location, such as at the C-terminus or the N-terminus. In various embodiments, the protein can include a nuclear localization signal (NLS). Any suitable NLS peptide sequence can be used. In some embodiments, simian virus SV40 NLS can be used, having a peptide sequence of 'PKKKRKV'. Any suitable technique can be used to add the organelle localization signal to the protein.

For example, to insert an NLS into the C-terminus of Cas9 protein, standard PCR based cloning procedures can be used. Briefly, a Cas9-E10 gene can be amplified with a reverse primer that carried the additional nucleotides coding for NLS peptide. The resultant Cas9-E10-NLS gene can be inserted into a pET28-b expressing vector and transformed into a BL21(DE3) Rosetta strain of bacteria. The protein expression and purification can be performed as described in the Examples.

Nucleic Acid Material.

The nanoparticle-protein complex can include a nucleic acid material. The nanoparticle-protein complex can have any suitable number of molecules of the nucleic acid material therein. In some embodiments, the nanoparticle-protein complex can have about 1 to about 10,000 molecules of the nucleic acid material, about 1 to about 5,000, about 500 to about 5,000, about 1,500 to about 2,500, or about 1, 2, 3, 4, 5, 10, 15, 20, 25, 50, 75, 100, 150, 200, 250, 500, 1,000, 1,200, 1,400, 1,600, 1,800, 2,000, 2,200, 2,400, 2,600, 2,800, 3,000, 3,500, 4,000, 4,500, 5,000, 6,000, 7,000, 8,000, 9,000, or about 10,000 or more molecules of the nucleic acid material. The nanoparticle-protein complex can include one kind of nucleic acid material, or more than one kind of nucleic acid material (e.g., more than one different kind of gRNA).

The nucleic acid material can have any suitable size. In some embodiments, in solution the nucleic acid material can have a largest dimension of about 0.5 nm to about 1000 nm, 0.5 nm to about 100 nm, or about 1 nm to about 50 nm, or about 0.5 nm or less, or about 1 nm, 2, 3, 4, 5, 6, 8, 10, 12, 14, 16, 18, 20, 25, 30, 35, 40, 45, 50, 55, 60, 65, 70, 75, 80, 85, 90, 95, or about 100 nm or more.

The nucleic acid material can be any suitable nucleic acid material that can be delivered using the nanoparticle-protein complex described herein. For example, the nucleic acid material can be at least one of DNA and RNA. The nucleic acid material can be at least one of mRNA (messenger RNA), rRNA (ribosomal RNA), 7SL RNA or SRP RNA (signal recognition particle RNA), tRNA (transfer RNA), tmRNA (transfer-messenger RNA), snRNA (small nuclear RNA), snoRNA (small nucleolar RNA), SmY (SmY RNA), scaRNA (small Cajal body-specific RNA), gRNA (guide RNA), catalytic RNA (e.g., ribozymes or catalytic RNAs, such as RNase P or RNase MRP), RNase P (ribonuclease P), RNase MRP (ribonuclease MRP), oligonucleotide RNA (e.g., RNA aptamers, or other oligonucleotide RNA such as gRNA or siRNA), Y RNA, TERC (telomerase RNA component), SL RNA (spliced leader RNA), aRNA or asRNA (antisense RNA), cis-NAT (cis-natural antisense transcript), crRNA (CRISPR RNA), lncRNA (long noncoding RNA), miRNA (microRNA), piRNA (piwi-interacting RNA), siRNA (small interfering RNA), tasiRNA (trans-acting siRNA), rasiRNA (repeat associated siRNA), and 7SK (7SK RNA). The nucleic acid material can be gRNA (guide RNA).

In some embodiments, the nucleic acid material and the protein can form a complex within the nanoparticle-protein complex, such as a 1:1 molar complex. The nucleic acid material and the protein can complex together in any suitable fashion.

The nucleic acid material can coordinate to the amine-group in the amine-containing ligand. For example, an ammonium ion in the amine-containing ligand can complex with a phosphate group in the nucleic acid material. In some embodiments, at least one end of the nucleic acid material includes a phosphate group.

Method of Intracellular Protein Delivery.

In various embodiments, the present invention provides a method of intracellular protein delivery. The method can include using any nanoparticle-protein complex to deliver at least some of the protein therein into a cell. The method can be any suitable method that results in the protein being delivered in to the cell. In some embodiments, the present invention provides a method of intracellular protein and nucleic acid material delivery, wherein the nucleic acid material is delivered into the cell with the protein.

In some embodiments, the method of intracellular protein delivery includes contacting a nanoparticle-protein complex with a cell. The nanoparticle-protein complex can be contacted to one cell or to multiple cells. The cell can be any suitable cell. The nanoparticle-protein complex can be any nanoparticle-protein complex described herein. The method can also include delivering the protein into the cell from the nanoparticle-protein complex. In embodiments including nucleic acid material in the nanoparticle-protein complex, the method can also include delivering then nucleic acid material into the cell from the nanoparticle-protein complex. The delivering can occur as a result of the contacting of the cell and the nanoparticle-protein complex. In some embodiments, the delivering occurs without any additional steps; e.g., the delivering can include simply allowing the nanoparticle-protein complex to release the protein (and the nucleic acid, if present in the nanoparticle-protein complex) into the cell. In some embodiments, a trigger can be applied (e.g., heat, chemical trigger, light, or vibration) to cause the delivering to occur. In some embodiments, the protein (and the nucleic acid, if present in the nanoparticle-protein complex) can be released into the cell cytoplasm. In some embodiments, the protein (and the nucleic acid, if present in the nanoparticle-protein complex) can be released within one or more specific organelles within the cell, such as within the nucleus.

Method of Forming a Nanoparticle-Protein Complex.

In various embodiments, the present invention provides a method of forming a nanoparticle-protein complex. The nanoparticle-protein complex can be any nanoparticle-protein complex described herein. The method can include combining a nanoparticle including an amine-containing ligand with a protein including a carboxylic acid-containing tag to form a self-assembled nanoparticle-protein complex. The nanoparticle including the amine-containing ligand can be any suitable nanoparticle including an amine-containing ligand described herein. The protein including the carboxylic acid-containing tag can be any protein including a carboxylic acid-containing tag described herein.

In some embodiments, the method can include combining a nanoparticle including an amine-containing ligand with a protein including a carboxylic acid-containing tag and a nucleic acid material to form a self-assembled nanoparticle-protein complex that includes the nucleic acid material.

Examples

Various embodiments of the present invention can be better understood by reference to the following Examples which are offered by way of illustration. The present invention is not limited to the Examples given herein.

Part I.

Example 1.1

Gold nanoparticles were engineered with an arginine ligand (ArgNP) to carry surface positive charges. Simultaneously, the protein was engineered with a 'ten glutamic acid tag' (E10-tag), either at the C-terminus or at the N-terminus of the protein to carry a multivalent, negatively charged tail. This co-engineering approach allowed fabrication of self-assembled NP-protein superstructures through electrostatic interactions. When the engineered NPs (diameter ~10 nm) and the 'E10-tag' protein (diameter ~1-20 nm) were mixed in a solution, they spontaneously self-assembled to form superstructures of the size of ~200 nm (diameter) (FIG. 1A, illustrating a scheme showing fabrication of NP-protein assemblies). Subsequently, upon incubation with cultured cells, these assemblies rapidly (in hours) delivered proteins into the cell-cytoplasm (FIG. 1B, a scheme showing use of NP-protein assemblies for intracellular protein delivery).

To investigate the generality of the approach, proteins were engineered having different physiochemical properties (i.e. size and charge). Both negatively charged (green fluorescent protein (GFP): pI=6.1, MW~27 kDa; mCherry: pI=6.2, MW~27 kDa) and positively charged proteins (Granzyme A: pI=9.2, MW~26 kDa; Cre recombinase: pI=9.6, MW~38.5 kDa; Cas9: pI=9, MW~158 kDa and Histone 2A: pI=10.9, MW~14 kDa) were used, at physiological conditions, with a range of molecular weights (MW). Upon addition of an E10-tag to the C- or N-terminus of each protein, they readily self-assembled with ArgNP, facilitating the protein delivery into HeLa cells (FIGS. 2A-F). FIGS. 2A-F illustrate intracellular delivery of various engineered 'E10-tagged' proteins into HeLa cells. Proteins other than GFP and mCherry were labeled with FITC.).

In addition, delivered proteins were efficiently released into the cell-cytoplasm, escaping the endosomes (FIGS. 2A-F). Moreover, proteins that carry a nuclear localization signal (Cas9), or that are intrinsically nuclear protein (histone 2A) can easily infiltrate into the nucleus. Similarly, granzyme A can penetrate into the nucleus by interacting with the nuclear envelope proteins. Taken together, these results demonstrated the ability of the method to deliver proteins into the destination organelles.

Example 1.2. Comparison of the NP-Based Method with Other Reported Methods

The delivered proteins in reported methods get trapped in the endosomes characterized by punctate structures, as shown in the photomicrographs of FIG. 3A (GFP-CPP) and FIG. 3B (+36-GFP). Cell penetrating peptides (CPP) are widely used for intracellular protein delivery, despite their inefficient protein delivery (endosomal entrapment) as shown in GFP-CPP. The +36-GFP was taken from Cronican J. J. et al, Chem Biol. 2011, 18(7), 833-838. FIG. 3C illustrates a photomicrograph of delivered proteins using GFP-E10/NP, showing accumulation of GFP in the cell-nucleus even when GFP was expressed by gene delivery.

Example 1.3. Other Proteins

Following is a list of proteins that were delivered into cells using the 'E-tagged' approach. All these proteins including GFP and Cas9 were delivered using a 'general protein delivery' strategy. An engineered gold nanoparticle (ArgNPs) was used for protein delivery. The protein to be delivered was engineered with a ten-glutamic acid tag (E10-tag). Any protein of interest can be delivered into cells using this E-tag approach. Thus this approach is a 'General Approach'. Further, the E-tag length may vary from one protein to another. In the Examples of Part I an E10 tag was used.

Example 1.3.1. Histone 2A: (MW=14 kDa, pI=10.9)

Histone 2A (H2A) is a major nuclear protein associated with nucleosomes that bind to DNA in the nucleus. H2A thus plays an important role in regulating chromatin function and dynamics Native H2A does not bind to ArgNPs due to its high positive charge at physiologically relevant conditions. However, the addition of an E10 tag to the C-terminus of H2A (H2A-E10) provided a negatively charged tail that facilitated the interaction with ArgNPs.

Figure 4C:
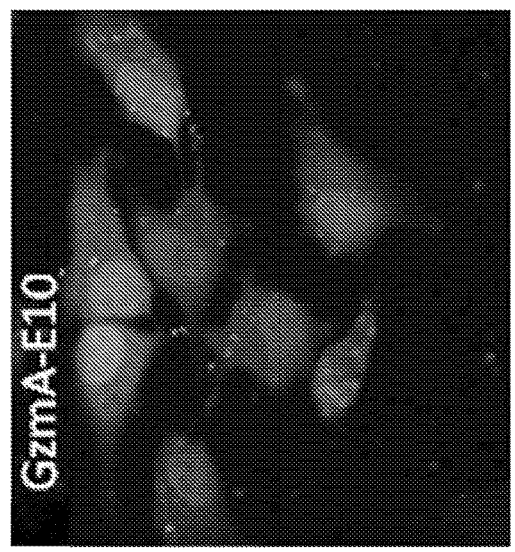
FIG. 4C illustrates a photomicrograph of intracellular delivery of GzmA-E10 via ArgNPs, in accordance with various embodiments.
Figure 4B:
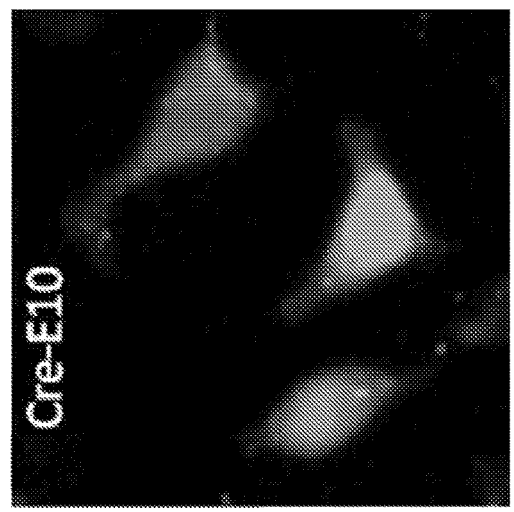
FIG. 4B illustrates a photomicrograph of intracellular delivery of Cre-E10 via ArgNPs, in accordance with various embodiments.
Figure 4A:
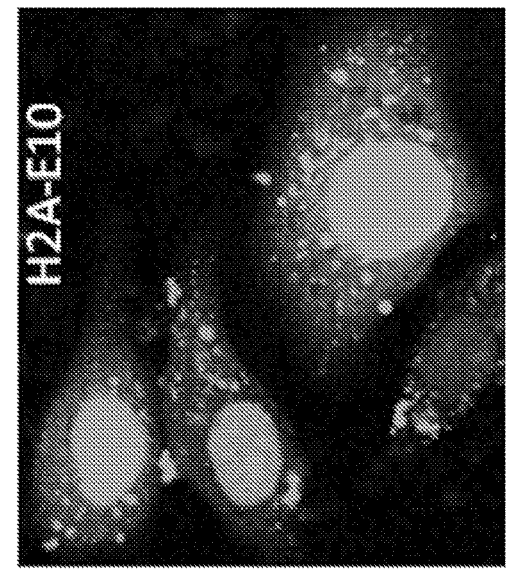
FIG. 4A illustrates a photomicrograph of intracellular delivery of H2A-E10 via engineered gold nanoparticles (ArgNPs), in accordance with various embodiments.

ArgNP-H2AE10 assemblies were first fabricated, followed by investigation of the delivery application. Briefly, ArgNP-H2AE10 assemblies were incubated with HeLa cells for 4 h. Confocal laser scanning microscopy (CLSM) imaging was used to monitor the H2A-E10 delivery. As shown in FIG. 4A, efficient H2A-E10 intracellular delivery was observed 4 h post incubation (FIG. 4A, illustrating a photomicrograph of intracellular delivery of H2A-E10 via ArgNPs). Importantly, H2A-E10 readily acquired access to the nucleus, owing to its inherent cryptic nuclear targeting signal.

Example 1.3.2. Cre Recobinase: (MW=38.5 kDa, pI=9.6)

Cre recombinase (Cre) protein is originally derived from a bacteriophage, and has been widely used for genetic recombination in mammalian cells. Cre mediated gene recombination is a standard tool for creating transgenic conditional gene knockout animals in laboratory. Similar to H2A, native Cre does not interact with ArgNPs due to its high positive charge.

An E10 tag was inserted to the N-terminus of Cre recombinase. Self-assembled ArgNP-CreE10 was then delivered into HeLa cells. Significantly, delivered Cre-E10 was evenly distributed into the whole cell, as evident from CLSM image (FIG. 4B, illustrating a photomicrograph of intracellular delivery of Cre-E10 via ArgNPs). These results confirm the direct intracellular protein delivery that did not get trapped in the endosomes.

Example 1.3.3. Granzyme A: (MW=26 kDa, pI=9.2)

Granzyme A (GzmA) is a major immune-modulatory enzyme in mammalian immune system. When a cytotoxic T-lymphocyte (CTL) binds to a target cell, CTL secretes GzmA, alongside other proteases to kill the target cell. Similar to H2A and Cre, native GzmA also does not bind to ArgNPs due to its high positive charge unless an E10 tag is added to the protein. A C-terminal E10 tag was added to GzmA (GzmA-E10). Subsequently, ArgNP-GzmAE10 assemblies were delivered into HeLa cells. After 4 h of incubation GzmA-E10 delivery was monitored by CLSM. As shown in FIG. 4C (illustrating a photomicrograph of intracellular delivery of GzmA-E10 via ArgNPs), a direct cytosolar protein delivery was observed, with prominent nuclear accumulation. This nuclear localization of GzmA- E10 was attributed to its ability to penetrate through the nuclear pore. Again, no endosomal entrapment was observed, suggesting a superior protein delivery method in comparison to many existing approaches.

Example 1.4. Synthesis of Nanoparticles with Arginine Ligand

Arginine functionalized gold nanoparticles (ArgNPs) were prepared according to Yang, X. C. et al. *Angew. Chem. Int. Ed. Engl.* 50, 477-481 (2011). Briefly, the arginine functionalized thiol ligand (HS-C11-TEG-NH-Arginine, FIG. 5A) was synthesized first. Then the ArgNPs were synthesized by place-exchange reaction. In a typical reaction, 10 mg of 1-pentanethiol protected gold nanoparticle (Au_C5) was dissolved in 10 mL distilled DCM and purged with argon for 10 min. Subsequently, 30 mg of HS-C11-TEG-NH-Arginine in 5 mL of methanol was added to the nanoparticle solution. The reaction mixture was allowed to stir for 2 days followed by removal of solvent mixture. The resulting black colored residue was then washed with a mixture of hexanes (90%) and DCM (10%) for 5 times to remove 1-pentanethiol and excess ligands. This ArgNP was dissolved in distilled water and purified by dialysis with skin membrane (10,000 MWCO) in distilled water for 12 h. Finally, molecular cut-off filtration (10,000 MWCO three times) was performed to ensure the high purity of ArgNPs.

Importance of the Ligand on the Surface of Gold Nanoparticles.

A single gold nanoparticle (AuNP) accommodates multiple arginine functionalized thiol ligands (HS-C11-TEG-NH-Arginine) on its surface (see FIG. 5B, illustrating a scheme showing place-exchange for the preparation of ArgNPs). The resultant AuNPs acquires multivalency, a prerequisite for strong supramolecular interaction with E10-tagged proteins. In contrast, if only a single ligand (FIG. 5A) is used, the interaction with E10-tagged proteins will not be strong enough for assembly formation, and thus for delivery applications.

Different components of the ligand are also important for the stability and function of the particles. As shown in FIG. 5B, the thiol (HS) group pins the ligand to the gold surface, the hydrophobic C11 group stabilizes the nanoparticle, the tetraethylene glycol (TEG) moiety confers biocompatibility to the particle, and finally the arginine head group dictates the interaction with E-tagged proteins though electrostatic/hydrogen bonding. The arginine head group is also important for protein delivery applications, as it helps interacting with the cell surface.

Example 1.5. Synthesis of Protein with Polyglutamic Acid Tag

GFP-E10 and mCherry-E10. Genetic engineering manipulation and protein expression were done according to standard protocols. GFP-E10 and mCherry-E10 were generated by PCR cloning respective gene along with codons for 10 glutamic acids at the C-terminus. The PCR amplified GFP-E10 and mCherry-E10 genes were inserted into a plasmid vector (pQE-80). Moreover, the N-terminus carried a 6xHis tag for purification purposes.

To produce recombinant proteins, plasmids carrying GFP-E10 or mCherry-E10 gene was transformed into *Escherichia coli* BL21(DE3) strain. A transformed colony was picked up to grow small cultures in 50 mL 2×YT media at 37° C. for overnight. The following day, 15 mL of grown culture was inoculated into one liter 2×YT media and allowed to grow at 37° C. until OD reached 0.6. At this point, the protein expression was induced by adding isopropyl-b-D-thiogalactopyranoside (IPTG; 1 mM final concentration) at 25° C. After 4-12 hours of induction, the cells were harvested and the pellets were lysed using a microfluidizer. His-tagged proteins were purified from the lysed supernatant using HisPur cobalt columns. The purity of native proteins was determined by 12% SDS-PAGE gel.

Purification of all other proteins followed the same procedure except different plasmid vectors, bacterial strain, and incubation conditions as mentioned below wherever are applicable:

Cas9-E10: pET28-b-Cas9-NLS-E10 plasmid (N-terminal E10 and C-terminal NLS) was expressed in BL21 (DE3) Rosetta bacterial strain for 16 h at 18° C. under 0.5 mM IPTG induction.

H2A-E10, Cre-E10, and GzmA-E10: pET21-b-H2A-E10 (C-terminal E10), pET21-b-Cre-E10 (N-terminus E10), and pET21-b-GzmA-E10 (C-terminus E10) were expressed in BL21 (DE3) Rosetta bacterial strain for 16 h at 25° C. under 1 mM IPTG induction.

Length of the E-tag is related to the protein delivery efficiency. The optimal length of the 'E-tag' for adding on a protein with efficient delivery was studied. GFP was chosen as the model protein. The length of E-tag was varied from GFP-E0 through GFP-E20. The delivery of these proteins was monitored by flow cytometry. An E10-tag (GFP-E10) was found to be efficient for the delivery application.

Part II. Engineered Self-Assembly of Nanoparticle-Cas9 Protein for Genome Editing.

Self-assembly between nanomaterials and bio-molecules can result in formation of larger structures. The assembled materials can acquire new functions that are not seen for individual components, and can have diverse applications in electronic and biomedical research. Examples of such assemblies include nanoparticle-DNA, and nanoparticle-proteins structures. Here, novel self-assemblies were fabricated between gold nanoparticles and proteins. Bacterially-derived CRISPR associated protein Cas9 was used. An oligo-glutamic acid tag was attached to Cas9 to carry a long negatively charged tail to form self-assembled structures with positively charged arginine functionalized gold nanoparticles. The utility of these assemblies was investigated by delivering Cas9 protein into cells for genome editing. Upon incubating the nanoparticle-Cas9 assemblies with cells, Cas9 protein was readily delivered, thus providing an efficient delivery vehicle for CRSIPR-Cas9 system for targeted genome editing.

Spontaneous organization of nanometer-sized building blocks into larger structures can generate new functional materials. To achieve such self-assembled materials, however, it is essential to engineer the individual components with appropriate interacting forces. In recent years, a wide variety of self-organized higher-order structures were made including nanoparticle-DNA, nanoparticle-protein, peptide-protein, and nucleic acids assemblies. Upon assembly formation, these structures can acquire novel or collective functions that are not exhibited by individual components. For example, several such self-assembled structures were used to confine enzymes, and deliver small and bio-molecular therapeutics including small interfering RNA (siRNA) and proteins in vivo, offering attractive opportunities for diseases treatment.

A bacterially derived clustered regularly interspaced short palindromic repeat (CRISPR) system has been adopted for efficient genome editing in diverse cell types. The CRISPR system is composed of two units: a Cas9 endonuclease protein, and a short guide-RNA (gRNA) molecule that ushers Cas9 to the target genomic loci. Once Cas9:gRNA complex is bound to the target DNA, Cas9 causes double stranded break (DSB) on the target gene. Consequently, cell's repair machinery deletes and inserts nucleotides at the DSB site, disrupting gene functions. Alternatively, a mutant gene can be repaired by providing a homology repair template alongside the CRISPR/Cas9 system; thus, making it an efficient genome editing tool.

With these features, CRISPR-Cas9 system has enormous potential to cure a variety of genetic diseases. Recently, the technology has been used to correct disease-causing mutations in mouse and in human cell lines for tyrosinemia, muscular dystrophy, cataract, and cystic fibrosis. However, despite its rapid success in genome editing there remains many challenges in delivering CRISPR/Cas9 system into cells. Delivery methods reported for CRISPR until now includes Cas9 gene, mRNA, and protein delivery. Cas9 gene delivery using cationic lipids results in long-term protein expression, thus increasing the possibilities of off-targeting effect. Likewise, mRNA delivery is limited by its poor stability and associated immunogenicity. On the other hand, 'one-time' protein delivery for genome editing offers improved specificity and broader applicability. However, reported Cas9 protein delivery methods utilized cell penetrating peptides, or cationic lipids that are prone to endosomal entrapment. Thus, an efficient Cas9 protein delivery into cells is in the utmost importance for targeted genome editing to cure genetic diseases.

In this study, it was hypothesized that an oligo-glutamic acid tag (E-tag) can be inserted in Cas9 such that the protein carries a multivalent negatively charged tail. The E-tag on Cas9 will facilitate its self-assembled structure formation with positively charged arginine functionalized gold nanoparticles (ArgNPs) for delivery application. Initially, a green fluorescent protein (GFP) was designed with a C-terminal E10 tag to investigate the self-assembled structure formation and the protein delivery application. GFP-E10 offered a colored (fluorescence) means to monitor the protein delivery dynamics. When mixed, GFP-E10 and ArgNPs readily self-assembled to form larger (~200 nm diameter) superstructures. Upon incubating these assemblies with cells, efficient cellular delivery of GFP-E10 was observed. Having confirmed the assembly formation and protein delivery application of GFP-E10 and ArgNPs, the Cas9 protein was then engineered with a similar E10 tag at the N-terminus. Likewise, Cas9-E10 formed self-assembled structures when mixed with ArgNPs. Subsequently, these structures were used to deliver Cas9-E10 to cells. Cellular delivery of Cas9-E10 offered an efficient means for targeted genome editing. Taken together, this E-tag approach provides a new avenue for fabricating higher order protein-nanoparticle structures with efficient protein delivery applicability.

Figure 6A:
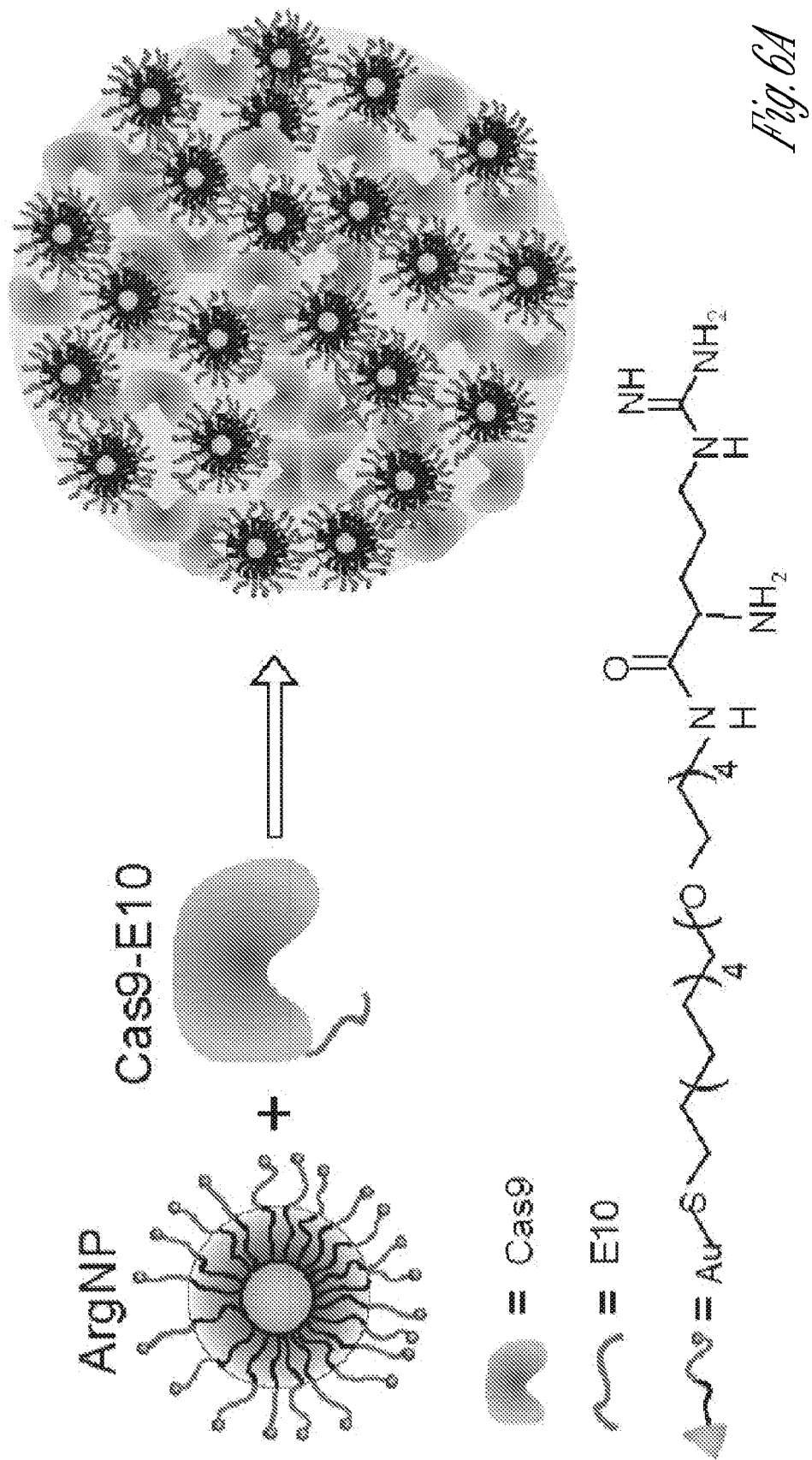
FIG. 6A illustrates a scheme showing electrostatic assembly of arginine functionalized gold nanoparticles with E-tagged Cas9, in accordance with various embodiments.

To this end, gold nanoparticles were synthesized functionalized with arginine ligands that can present multivalent positive charges on their surface. FIG. 6A illustrates a scheme showing electrostatic assembly of arginine functionalized gold nanoparticles with E-tagged Cas9. FIG. 6B illustrates a scheme showing delivery of E-tagged Cas9 into cells using arginine functionalized gold nanoparticles with E-tagged Cas9. In these studies, multivalent arginine ligands on nanoparticles surface help interacting with negatively charged cell membrane, presumably through electrostatic interaction. Synthesized ArgNPs harbored a 2-nm (diameter) gold core. The particles were soluble in water or in physiological buffer with no detectable cytotoxicity, resulting in properties that are desirable for delivery applications.

Figure 7C:
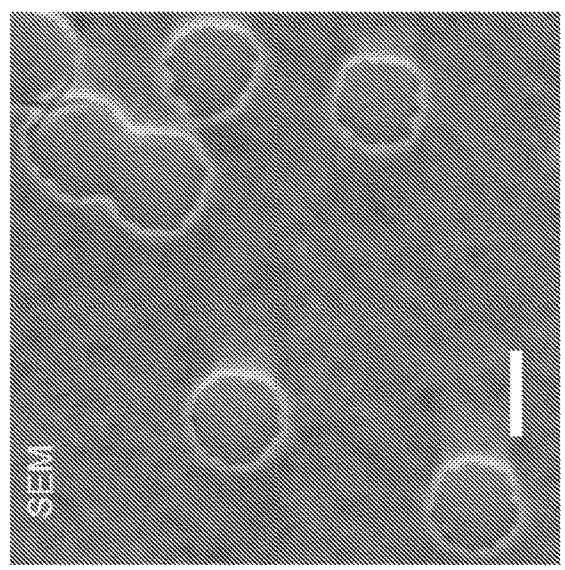
FIG. 7C illustrates a SEM image of ArgNP-GFPE10 self-assembled superstructures, in accordance with various embodiments.
Figure 7B:
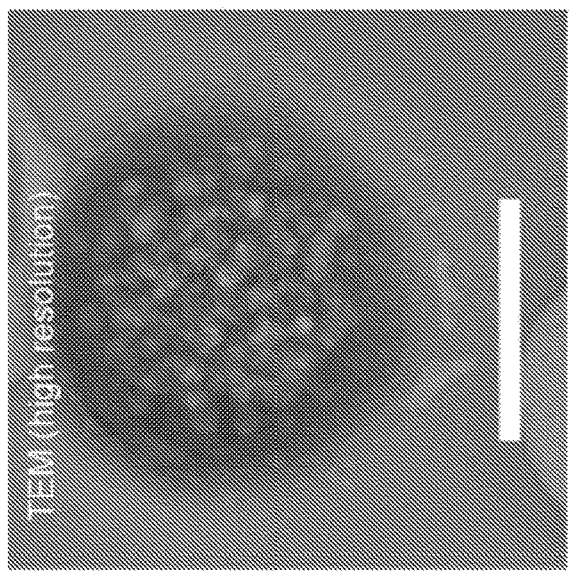
FIG. 7B illustrates a TEM image at higher resolution of ArgNP-GFPE10 self-assembled superstructures, in accordance with various embodiments.
Figure 7A:
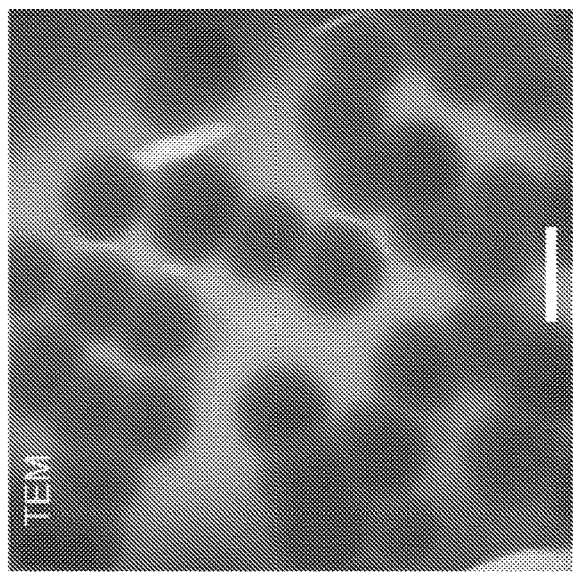
FIG. 7A illustrates a TEM image of ArgNP-GFPE10 self-assembled superstructures, in accordance with various embodiments.
Figure 7D:
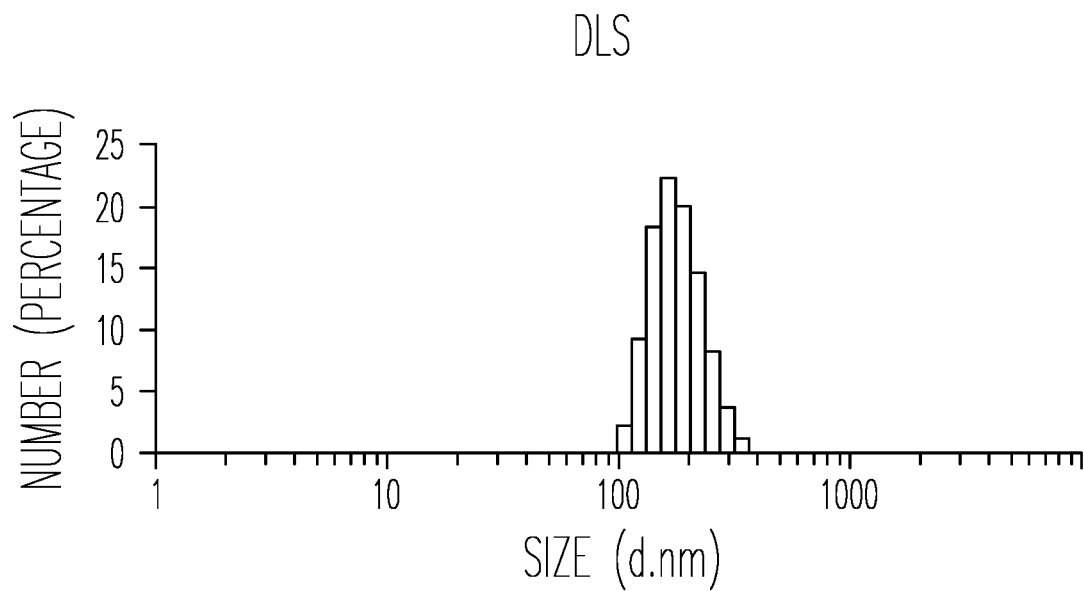
FIG. 7D illustrates dynamic light scattering (DLS) data of ArgNP-GFPE10 self-assembled superstructures, in accordance with various embodiments.
Figure 7E:
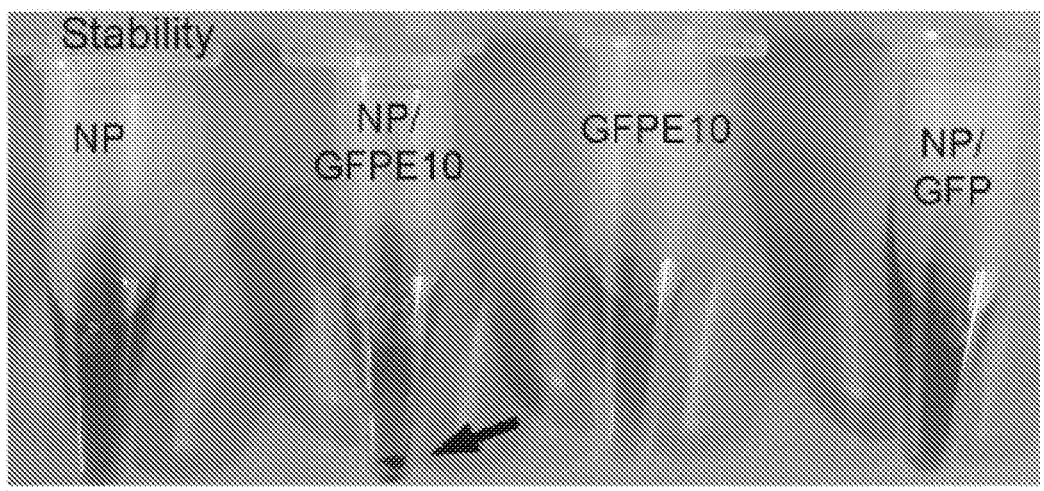
FIG. 7E illustrates a photograph of the assembled ArgNP-GFPE10 structures after centrifuging at 3000 rpm, in accordance with various embodiments.
Figure 7H:
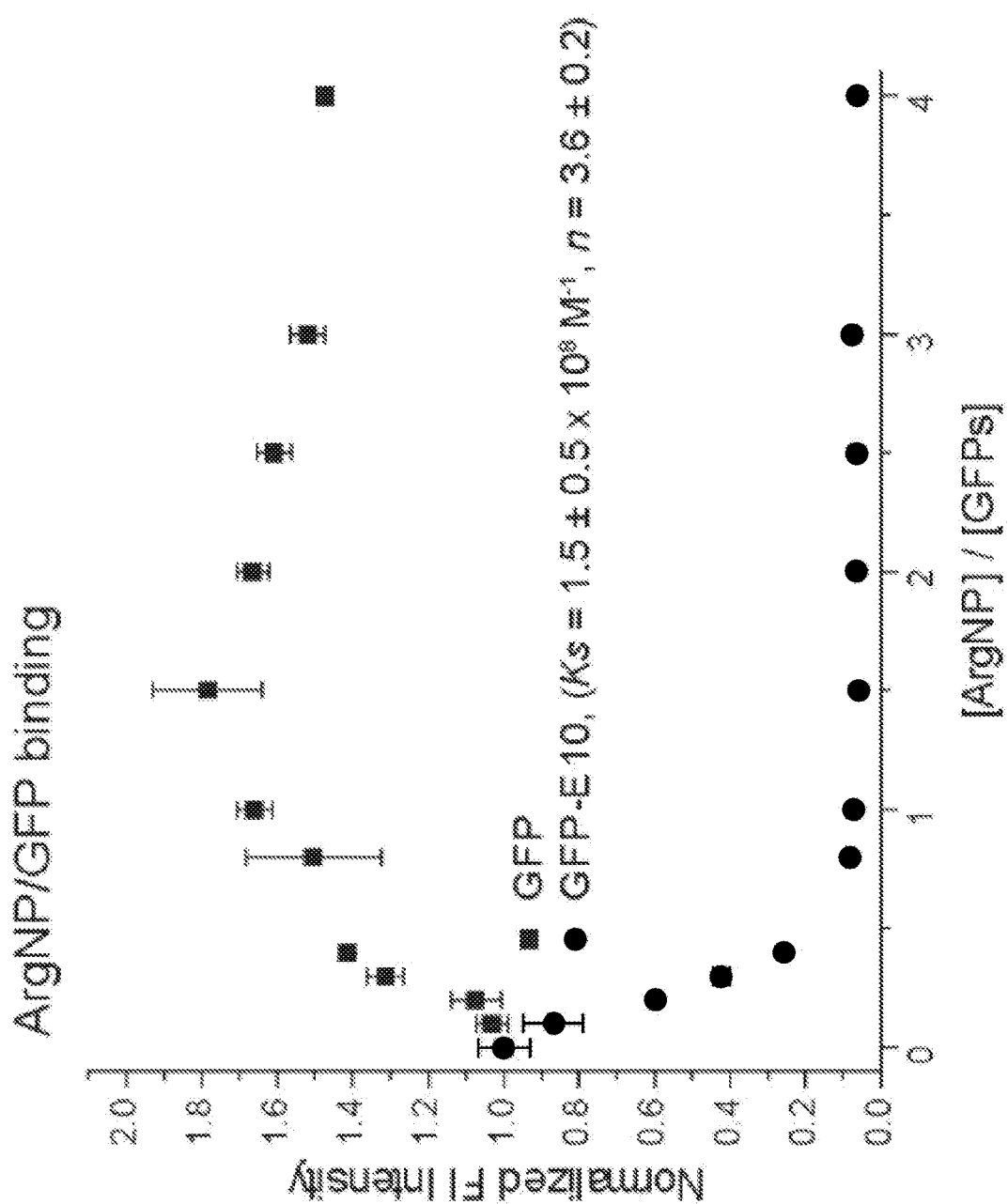
FIG. 7F illustrates fluorescence titration curves showing a strong binding between ArgNPs and GFP-E10 at physiologically relevant conditions, in accordance with various embodiments.

The initial studies were focused on fabricating self-assembled structures between ArgNPs and E-tagged proteins. GFP (molecular weight MW=27 kDa) was chosen as the model protein, as GFP offers a facile way to fluorescently monitor the delivery applications of the assemblies. Initially, GFPs were engineered with different length of C-terminal E-tags (varying from E0 to E20). Among these, GFP-E10 was initially found to be the optimum for assembly formation and delivery applications. Desired self-assemblies were fabricated by mixing ArgNPs and GFP-E10 at various molar ratio in physiological buffer (1×PBS, pH 7.4) or in or cell culture media. Following this step, the assemblies were characterized after incubating the mixture at room temperature for 10 min. Transmission electron microscope (TEM) and dynamic light scattering (DLS) results suggested the formation of self-assembled superstructures between ArgNP and GFP-E10 as shown in FIGS. 7A, 7B, and 7D. FIG. 7A illustrates a TEM image of ArgNP-GFPE10 self-assembled superstructures, with the scale bar indicating 200 nm. FIG. 7B illustrates a TEM image at higher resolution of ArgNP-GFPE10 self-assembled superstructures, with the scale bar indicating 200 nm. FIG. 7D illustrates dynamic light scattering (DLS) data of ArgNP-GFPE10 self-assembled superstructures. The hydrodynamic diameter of these superstructures were 216.6±nm compared to individual ArgNPs (10 nm) and GFP-E10 (4.5 nm), indicating the incorporation of a large number of nanoparticles and proteins into the self-assembled structures. Interestingly, high resolution TEM images indicated the dense packing of granular proteins into the self-assembled superstructures (FIG. 7B). The optimal molar ratio for assembly formation was determined to be 1:3 (ArgNP/GFP-E10), as uniform superstructures were observed by TEM and scanning electron microscope (SEM) studies at this ratio (FIG. 7C, illustrating a SEM image of ArgNP-GFPE10 self-assembled superstructures, with the scale bar indicating 200 nm). Additionally, no free ArgNPs were observed on the TEM grid at this optimized ratio, indicating complete incorporation of nanoparticles into the structures. The electrokinetic potential of these structures were −3.1 mV in comparison to individual ArgNPs (+18.2 mV) and GFP-E10 (−7 mV), thus suggesting the incorporation of both nanoparticles and proteins into the structures. Furthermore, GFP-E10, but not GFP was completely pelleted down by centrifugation (3000 rpm, 5 min) after mixing with ArgNPs, confirming the self-assembled superstructure formation (FIG. 7E, illustrating a photograph of the assembled ArgNP-GFPE10 structures after the centrifuging).

Further evidence of a strong interaction between the ArgNPs and GFP-E10 was achieved by fluorescence titration studies (FIG. 7F), where GFP-E10 was titrated against a varying concentration of nanoparticles at physiologically relevant electrolyte concentration. FIG. 7F illustrates fluorescence titration curves showing a strong binding between ArgNPs and GFP-E10 at physiologically relevant condition. The binding constant (Ks) and the molar binding ratio (n) were determined using a previously reported method. Significantly, the molar binding ratio was n=1:3.6 (ArgNP/GFP-E10) consistent with the complete incorporation ratio obtained from TEM and SEM characterization. A high binding constant ($K_s=1.5\pm0.5\times10^8 M^{-1}$) was observed, indicating the strong multivalent electrostatic interaction between ArgNPs and GFP-E10. As expected, no noticeable interaction was observed for GFP without an E-tag.

Figure 8A:
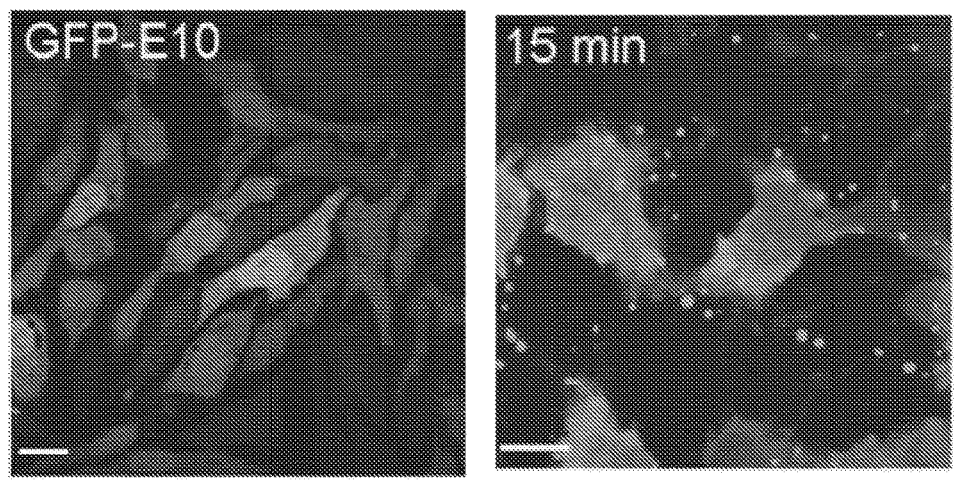
FIG. 8A illustrates confocal microscopy image of HeLa cells with GFP-E10 delivered via ArgNP-GFPE10 structures after 1 h incubation, in accordance with various embodiments.
Figure 8B:
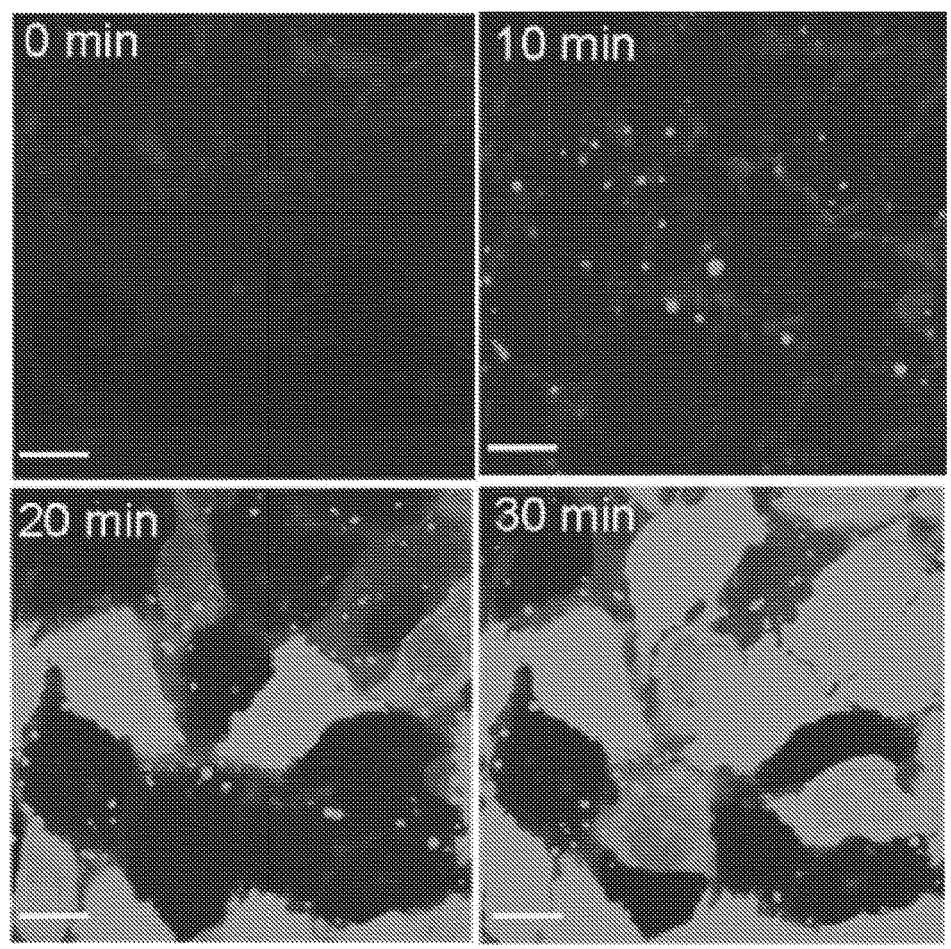
FIG. 8B illustrates time lapse imaging of GFP-E10 delivered via ArgNP-GFPE10 structures in HeLa cells, in accordance with various embodiments.
Figure 8C:
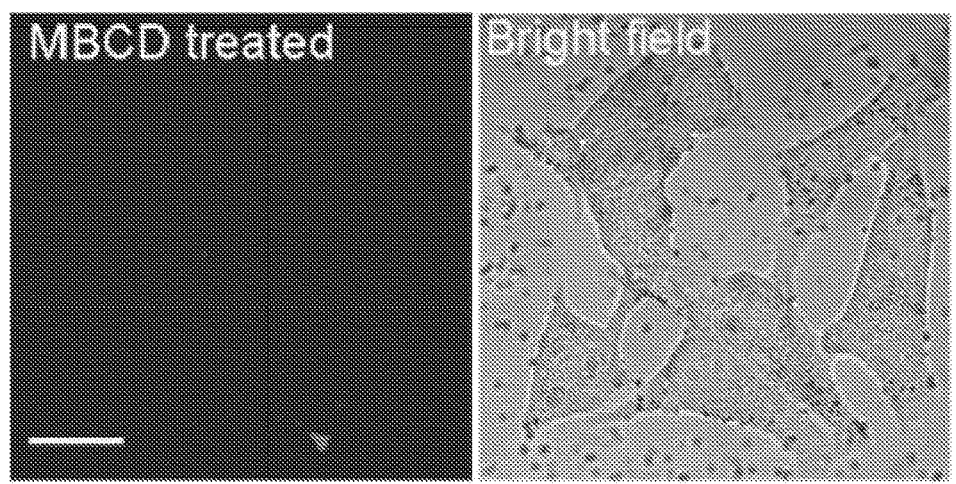
FIG. 8C illustrates GFP-E10 delivery via ArgNP-GFPE10 structures in membrane cholesterol depleted (MBCD treated) cells, in accordance with various embodiments.
Figure 8D:
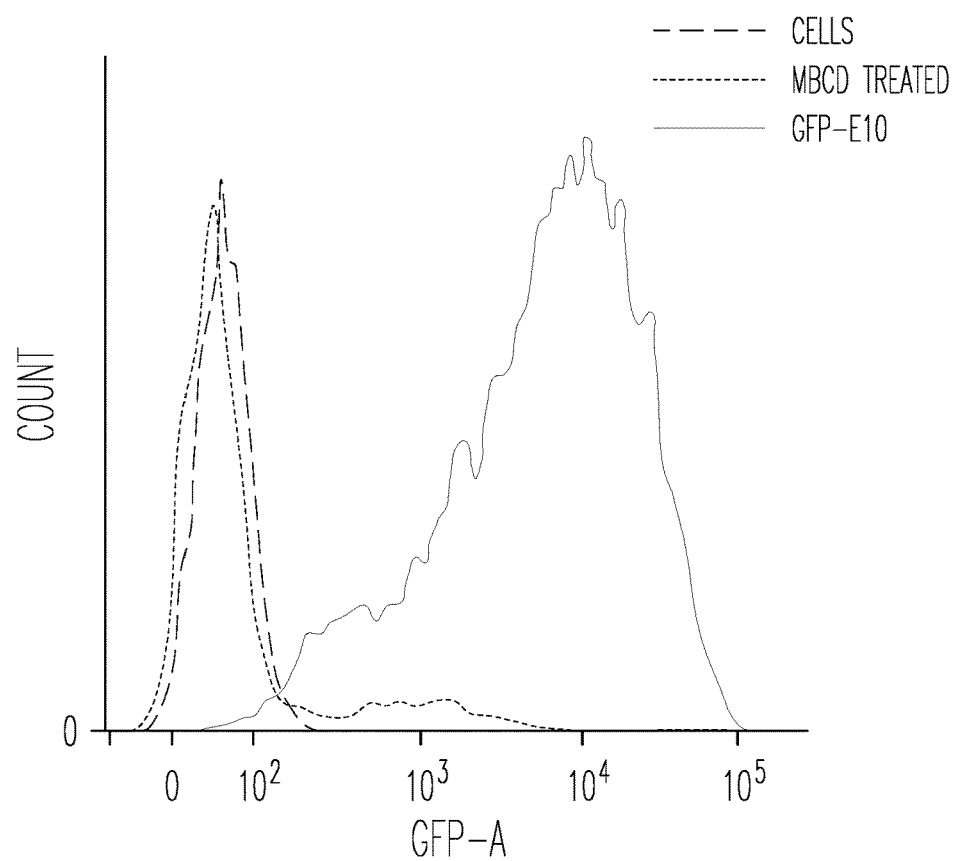
FIG. 8D illustrates flow cytometric measurement showing GFP-E10 delivery via ArgNP-GFPE10 structures in MBCD treated and untreated cells, in accordance with various embodiments.

The high stability of these self-assembled structures under physiological conditions makes them potentially applicable as delivery vehicles for proteins. Previous studies suggested that self-assembled ArgNPs on the surface of oil droplets can efficiently deliver siRNA directly into the cytosol of a cell. This prompted use of the nanoparticle-protein assemblies to investigate their delivery applicability. To this end, ArgNP-GFPE10 assemblies were incubated with HeLa cells in cultured media. The cellular uptake of GFP-E10 was monitored using confocal laser scanning microscopy (CLSM) and flow cytometry. Successful GFP-E10 delivery into cells was obtained after 1 h of incubation as shown in FIGS. 8A and D. FIG. 8A illustrates confocal microscopy image of HeLa cells with GFP-E10 delivered via ArgNP-GFPE10 structures after 1 h incubation, with the scale bar indicating 20 microns. FIG. 8D illustrates flow cytometric measurement showing GFP-E10 delivery via ArgNP-GFPE10 structures in MBCD treated and untreated cells.

In comparison, no delivery was observed when only GFP was mixed with ArgNPs. Significantly, delivered GFP-E10 was evenly distributed in the whole cell with prominent nuclear accumulation due its free diffusion across the nuclear pore. More importantly, delivered GFP-E10 was not trapped into the endosomes, unlike many other delivery vehicles including supper positive charged GFP, cell penetrating peptide, or polymer based vehicles. The delivery efficiency of GFP-E10 was dictated by the assembly formulation, with highest GFP intensity (50,000 fold higher than the controls) observed at 250 nM of ArgNPs and 750 nM of GFP-E10, as determined by flow cytometry analysis (FIG. 8D).

Live cell video imaging was performed to study the intracellular release-dynamics of GFP-E10. Time lapse fluorescence imaging video was recorded immediately after the addition of the ArgNP-GFPE10 assemblies into HeLa cells at 1 min intervals. As shown in FIG. 8B, the release of GFP-E10 was observed at 15 min post incubation. FIG. 8B illustrates time lapse imaging of GFP-E10 delivered via ArgNP-GFPE10 structures in HeLa cells, with the scale bar indicating 20 microns, and with "0 min" indicating the starting point of the incubation. Complete protein delivery was achieved after 40 min of post incubation, demonstrating a remarkably fast delivery of GFP-E10 using these assemblies. The instantaneous release of GFP-E10 into the whole cell further suggested that the protein payload is directly released from the cell membrane and does not undergo through endocytosis.

Such nanoparticle mediated biomolecular delivery can occur through membrane fusion mechanisms. Previous work on ArgNPs-mediated siRNA delivery indicated that the depletion of membrane cholesterols can block the delivery process. To investigate whether a similar mechanism is involved in GFP-E10 delivery, HeLa cells were pretreated with methyl-beta-cyclodextrin (MBCD), a known agent that depletes cellular membrane cholesterols. After MBCD treatment, HeLa cells were incubated with ArgNP-GFPE10 assemblies and monitored by CLSM and flow cytometry. As shown in FIGS. 8C and D, MBCD treatment completely inhibited GFP-E10 delivery into cells, suggesting a cholesterol dependent membrane-fusion delivery mechanism. FIG. 8C illustrates GFP-E10 delivery via ArgNP-GFPE10 structures in membrane cholesterol depleted (MBCD treated) cells, with the scale bar indicating 20 microns. The arrow shows the nanoparticle-protein superstructures attached to the cell membrane after treating the cells with MBCD. These studies collectively confirmed that the nanoparticle-protein assembly mediated GFP-E10 delivery occurs through a membrane fusion process, bypassing cellular endocytosis.

Having established the effective delivery of E10-tagged GFP mediated by ArgNP-GFPE10 self-assemblies, the delivery of CRISPR/Cas9 system was investigated for genome editing using a similar approach. A recombinant Streptococcus pyogenes(Sp) Cas9 protein was cloned harboring an E10 tag at the N-terminus. The resultant Cas9-E10 exhibited a theoretical pI=8.8 in comparison to pI=9.07 of the native Cas9, still remaining positively charged at physiological pH 7.4. However, localized multivalent negative charges on E10 tag was sufficient for facilitating the assembly formation between Cas9-E10 and ArgNPs as evident from binding studies. In addition to an E10 tag, a nuclear localization signal (NLS) was added to the C-terminus of Cas9 to target Cas9 protein into the cellular nucleus for gene editing.

Self-assemblies between ArgNPs and Cas9-E10 were fabricated and characterized similar to that of GFP-E10. The optimum ratio of ArgNP/Cas9-E10 was 1:0.4 (obtained from binding studies), unlike 1:3 of ArgNP/GFP-E10. This decrease in protein amount is presumably due to a larger size of Cas9-E10 (MW=160 kDa). Likewise, a larger assembly size was observed (~317±nm in diameter) as evident from TEM and DLS measurements.

Figure 9A:
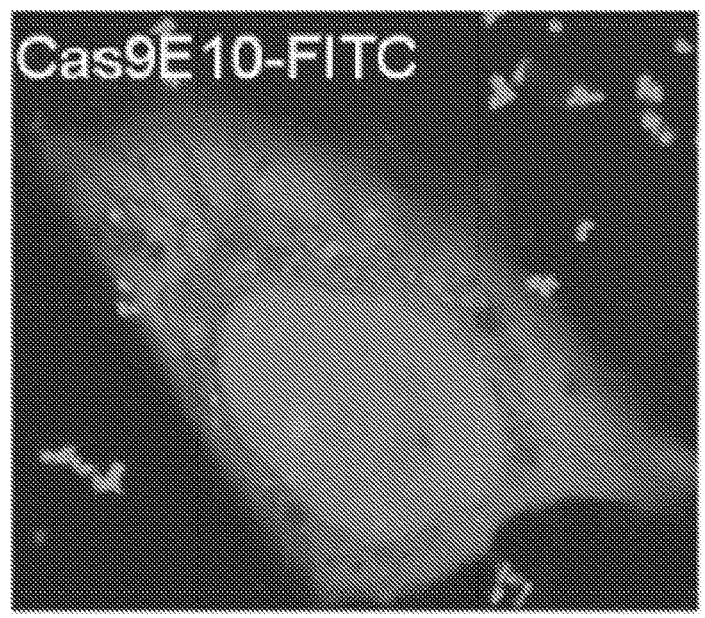
FIG. 9A illustrates confocal microscopy image of FITC-Cas9-E10 delivery into HeLa cells via ArgNP-Cas9E10 structure, in accordance with various embodiments.
Figure 9B:
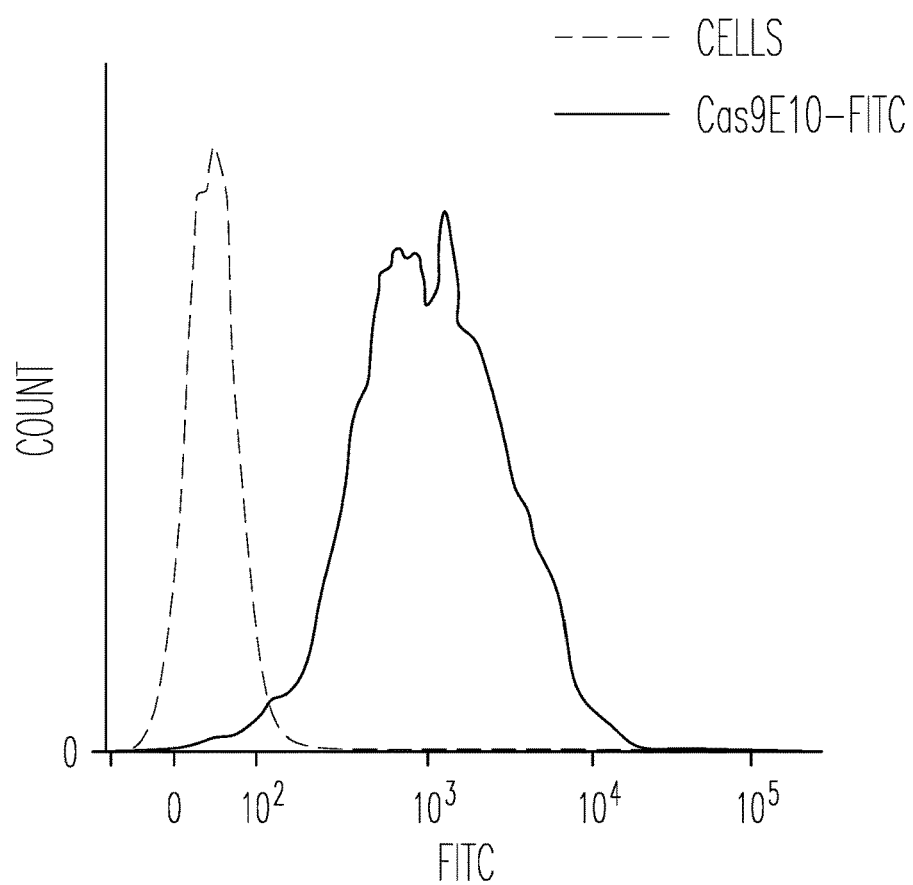
FIG. 9B illustrates flow cytometric analysis of FITC-Cas9-E10 delivery into HeLa cells via ArgNP-Cas9E10 structure, in accordance with various embodiments.

Following the fabrication of ArgNP-Cas9E10 self-assemblies, protein delivery efficiencies were investigated. In these studies, fluorescein isothiocyanate (FITC) labeled Cas9-E10 (50 nM) was incubated with ArgNP (125 nM) in cell culture media prior to the cellular delivery. Subsequently, delivery of FITC-Cas9-E10 was monitored at different time point using CLSM and flow cytometry. As shown in FIGS. 9A-B efficient delivery of Cas9-E10 into HeLa cells was observed after 4 h, confirmed by both CLSM and flow cytometry. FIG. 9A illustrates confocal microscopy image of FITC-Cas9-E10 delivery into HeLa cells via ArgNP-Cas9E10 structure. FIG. 9B illustrates flow cytometric analysis of FITC-Cas9-E10 delivery into HeLa cells via ArgNP-Cas9E10 structure. Significantly, FITC fluorescence was distributed through the whole cell, with prominent accumulation in the nucleus. This nuclear localization can be attributed to the insertion of the NLS sequence at the C-terminus of Cas9 protein. Importantly, the delivery of Cas9-E10 protein into the nucleus is a prerequisite for efficient genome editing. When HeLa cells were pretreated with MBCD, Cas9-E10 protein delivery was completely inhibited, again suggesting a membrane-fusion protein delivery mechanism. These studies collectively suggested an efficient Cas9-E10 delivery that bypasses endo/lysosomal entrapment.

Figure 9C:
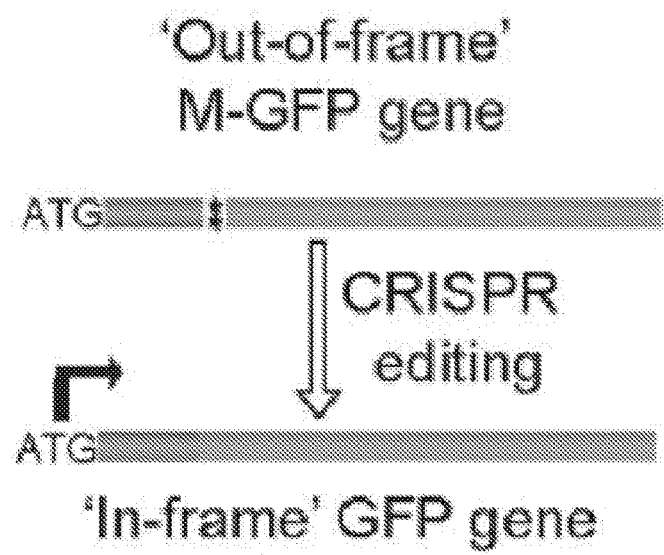
FIG. 9C illustrates a schematic showing CRISPR mediated targeted gene editing of M-GFP construct, in accordance with various embodiments.

After demonstrating successful cellular delivery Cas9-E10 protein, its genome editing efficacy was next investigated. Conventionally, CRISPR-mediated gene disruption/editing are tested by a Surveyor nuclease based insertion and deletion (indel) experiment. However, such an experiment requires isolating the whole genome from the treated cells and depends on the efficiency of the surveyor nuclease. Alternatively, a cell line that can exhibit 'turn on' fluorescence after CRISPR-mediated targeted gene editing is more desirable due to its rapid and non-destructive approach. To this end, a reporter HeLa cell line was generated that can harbor a mutant green fluorescence protein (M-GFP) gene. Usually GFP expression is 'off' in these cells, but turns on after appropriate editing of the mutant gene. The M-GFP gene was designed by placing 23 nucleotides (20 nt for protospacer+3 nt for PAM) at the beginning of the GFP open reading frame (ORF) (FIG. 9C, illustrating a schematic showing CRISPR mediated targeted gene editing of M-GFP construct). Thus, the resultant out-of-frame transcript codes for a non-functional GFP protein. Meanwhile, a gRNA was designed for the CRISPR system to target the additional nucleotides inserted at the beginning of the GFP ORF. Targeted editing of M-GFP gene was expected after delivering Cas9-E10 and the gRNA, a random indel process can produce an in-frame GFP transcript, thus expressing a functional reporter protein.

Figure 9D:
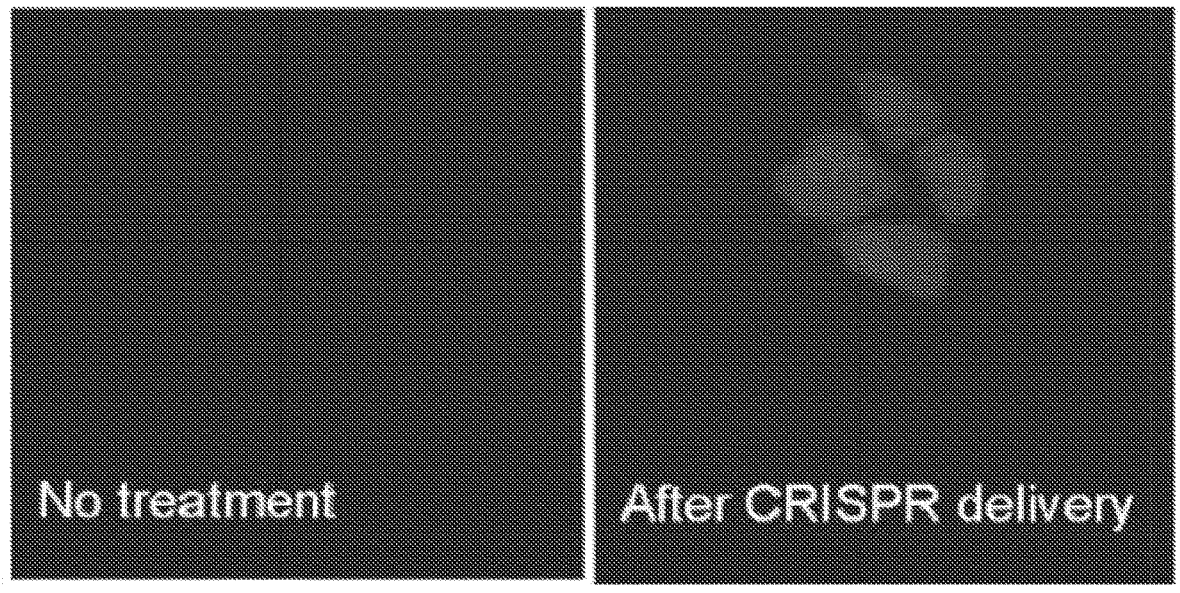
FIG. 9D illustrates confocal microscopy image of cells after delivering Cas9-E10 and gRNA via ArgNP-Cas9E10 structure for editing M-GFP gene, in accordance with various embodiments.
Figure 9E:
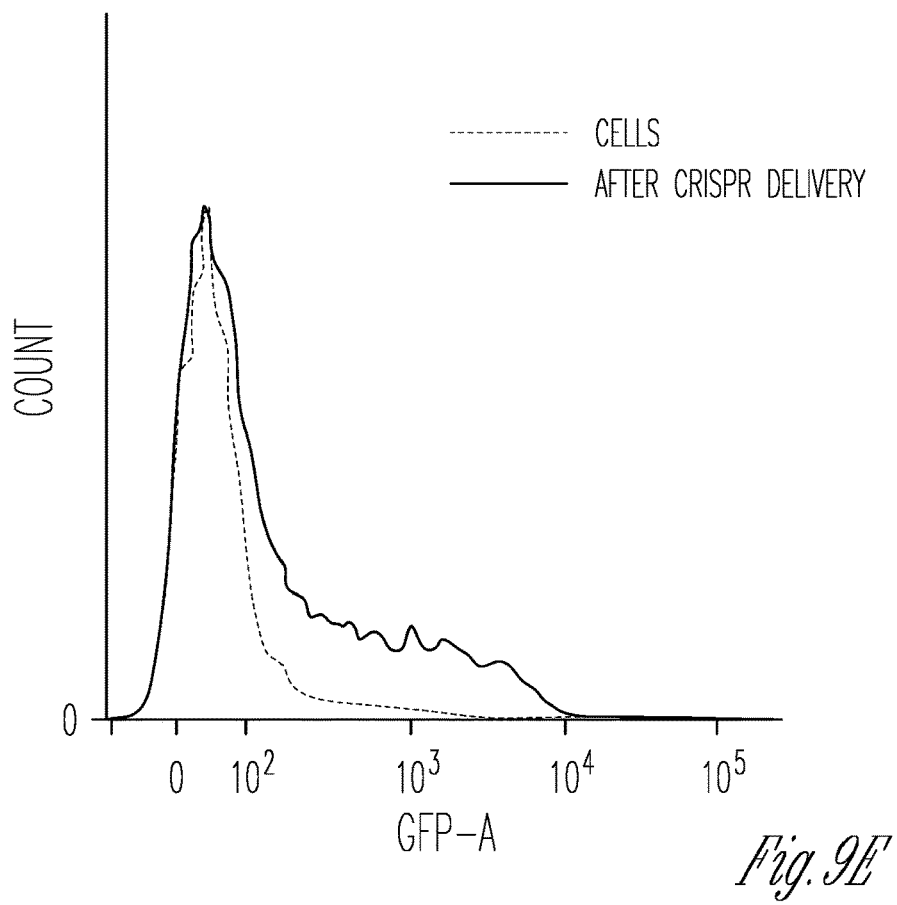
FIG. 9E illustrates flow cytometric analysis of cells after delivering Cas9-E10 and gRNA via ArgNP-Cas9E10 structure for editing M-GFP gene, in accordance with various embodiments.

ArgNP-Cas9E10 assemblies were then delivered into the HeLa cells targeting M-GFP gene. In these experiments, the assemblies were incubated with the cells for 4 h, followed by delivering the gRNA with a cationic lipid carrier. Genome editing efficiency was evaluated after 48 h using flow cytometry and CLSM. As evident from FIG. 9E, flow cytometry results suggested that the GFP positive cells increased by 15% for the Cas9-E10 delivered cells compared to the untreated controls. FIG. 9E illustrates flow cytometric analysis of cells after delivering Cas9-E10 and gRNA via ArgNP-Cas9E10 structure for editing M-GFP gene. On the other hand, only ArgNP-Cas9E10 assemblies and a scramble gRNA did not show any gene editing, similar to the untreated controls. Importantly, this efficiency of gene editing was superior to previously reported CRISPR delivery methods. Likewise, CLSM results showed efficient editing of M-GFP gene as evident from the appearance of GFP positive cells in the Cas9-E10 delivered cells (FIG. 9D, illustrating confocal microscopy image of cells after delivering Cas9-E10 and gRNA via ArgNP-Cas9E10 structure for editing M-GFP gene). These results collectively showed the efficient genome editing capability of ArgNP-Cas9E10 self-assemblies upon delivering into cells.

In summary, a strategy has been developed to construct self-assembled structures through electrostatic interactions between engineered gold nanoparticles and Cas9 protein guided by a polyvalent glutamic acid tail. Formation of controlled size assemblies helped delivering CRISPR/Cas9 into cells, thus providing an efficient way of targeted genome editing with no detectable carrier toxicity. The development of such nanoparticle based carrier assemblies for CRISPR/Cas9 system can facilitate the rapidly growing genome editing research for curing diverse genetic diseases.

Part III. Delivery of Cas9:gRNA Using a Single Nanoassembly Vehicle.

A CRISPR system was used including a Cas9 protein and a gRNA molecule. The gRNA can guide the Cas9 protein to the target DNA for gene editing. The gRNA was about 60-100 nucleotides long, and can be designed based on the target gene. The gRNA was composed of a variable region (20 nucleotides) complementary to the target gene and a constant region (tracRNA) that helps binding with Cas9 protein.

Construction of NP-Cas9E10:gRNA Nanoassembly.

First Cas9E10:gRNA complex was made by mixing Cas9E10 protein and the gRNA in equimolar ratio in 1×PBS. The mixture was then incubated at room temperature for 30 minutes. ArgNPs (250 nM) were then added to the Cas9E10:gRNA complex (50 nM). Subsequently nanoassemblies were allowed to form spontaneously for 10 minutes and immediately used for cellular delivery application.

Delivery Method.

Following the fabrication of NP-Cas9E10:gRNA nanoassemblies they were directly transferred to cultured HeLa cell for cellular Cas9E10:gRNA delivery studies. Briefly, 500 uL of the nanoassemblies (in DMEM media) was directly added to HeLa cells grown in a 24-well plate for overnight. Subsequently, cells were then incubated with these nanoassemblies for 4 h at 37° C. at 5% $CO_2$, then washed, and replaced with fresh media.

Editing Method.

For gene editing, NP-Cas9E10:gRNA nanoassemblies were delivered into M-GFP transgenic HeLa cell line. A M-GFP HeLa cell line was developed. A gRNA was designed to target the M-GFP gene. After delivering NP-Cas9E10:gRNA nanoassemblies into M-GFP HeLa cells, the editing efficiency was determined after 48 h post incubation using flow cytometry.

Figure 10A:
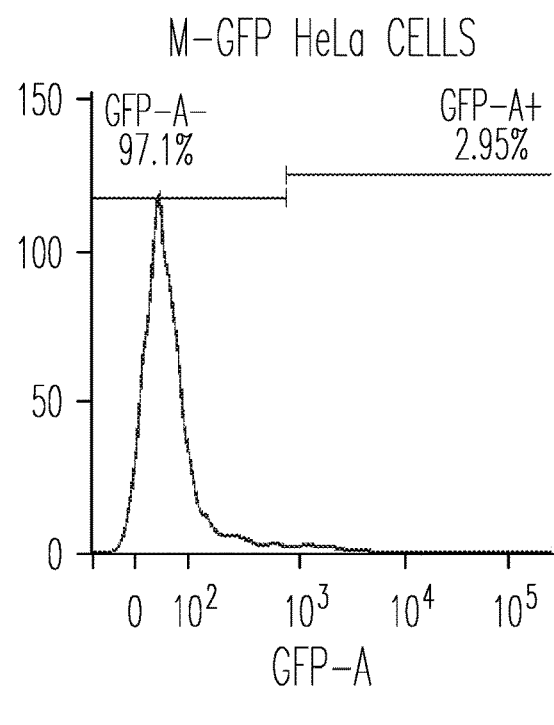
FIG. 10A illustrates flow cytometric fluorescence intensity of M-GFP HeLa cells before NP-Cas9E10:gRNA delivery, in accordance with various embodiments.
Figure 10B:
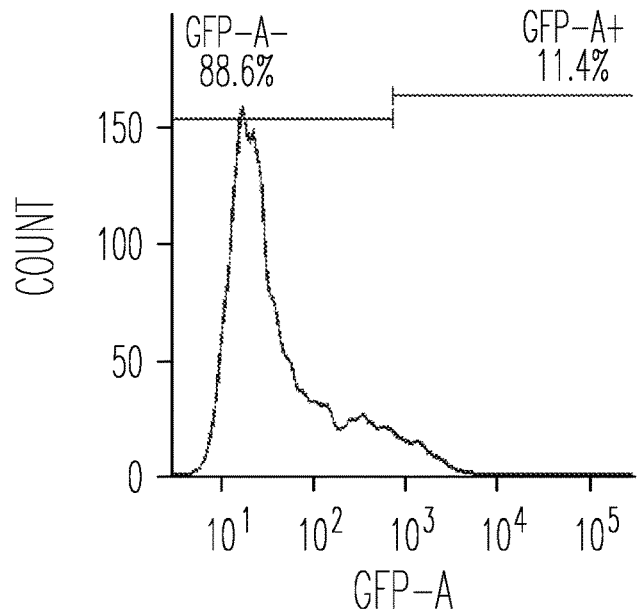
FIG. 10B illustrates flow cytometric fluorescence intensity of M-GFP HeLa cells after NP-Cas9E10:gRNA delivery, in accordance with various embodiments.
Figure 10C:
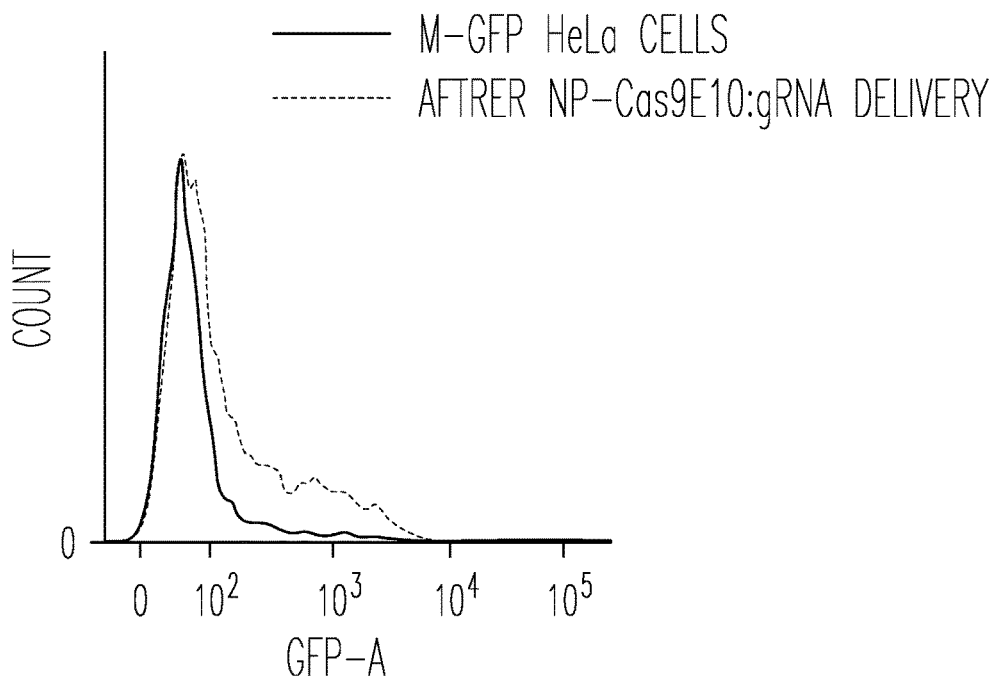
FIG. 10C illustrates a comparison of fluorescence intensity before and after NP-Cas9E10:gRNA delivery, in accordance with various embodiments.

FIG. 10A illustrates flow cytometric fluorescence intensity of M-GFP HeLa cells before NP-Cas9E10:gRNA delivery. FIG. 10B illustrates flow cytometric fluorescence intensity of M-GFP HeLa cells after NP-Cas9E10:gRNA delivery. FIG. 10C illustrates a comparison of fluorescence intensity before and after NP-Cas9E10:gRNA delivery. Genome editing efficiency that was measured after 48 h of post-nanoassembly incubation by flow cytometry indicated that the GFP positive cells increased by ~8% for the Cas9-E10:gRNA delivered cells compared to the untreated controls. On the other hand, only NP-Cas9E10 assemblies and nanoassemblies with a scramble gRNA did not show any gene editing, similar to the untreated controls. Importantly, this efficiency of gene editing was similar to previously reported CRISPR delivery methods. Likewise, Confocal Laser Scanning Microscope (CLSM) results showed efficient editing of M-GFP gene. These results collectively showed the efficient genome editing capability of NP-Cas9E10:gRNA self-assemblies upon delivering into cells.

Part IV. Engineered Cas9-Ribonuleoprotein for Highly Efficient Direct Cytoplasmic/Nuclear Delivery.

Application of CRSIPR/Cas9 technology in gene editing, transcriptional gene activation, and imaging chromosomal dynamics requires efficient delivery of the CRISPR components, with minimal unwanted gene targeting. Such off-targeting can be minimized by transient delivery of CRISPR systems into host cells including direct delivery of the Cas9 protein. Despite a few reports on Cas9 protein delivery strategies, efficient delivery into cytoplasm/nucleus remains a challenge. Reported methods are limited by the entrapment of Cas9 protein in the endosomes that result in 'wasting' the delivered protein: hence they were inefficient. Here an alternative direct cytoplasmic/nuclear delivery of Cas9 protein is reported alongside a guide RNA (sgRNA) across the cell-membrane resulting in remarkably high delivery efficiency. Such 'remarkably' high delivery was achieved via a rational and simultaneous engineering of the Cas9 proteins and the carrier gold nanoparticles. Engineered Cas9 protein and the sgRNA formed self-assembled nanoassemblies with gold nanoparticles that delivered Cas9:sgRNA into cell cytoplasm through a membrane fusion mechanism, avoiding endosomal entrapment. Thus, the approach provides a major advance in Cas9 protein delivery that may broaden the applicability of CRISPR/Cas9 technology.

Bacterially derived CRISPR system (Clustered Regularly Interspaced Short Palindromic Repeat) has been adopted as a versatile tool for genome editing, transcriptional control of genes, and visualizing genome dynamics Due to its remarkable genome editing efficiency, CRISPR/Cas9 system holds great promises for curing human genetic diseases. Recently, in efforts to cure genetic diseases, this system has been applied to correct a variety of disease-causing mutations in cultured cells and in animal models. In these studies, various gene delivery strategies for CRISPR/Cas9 have been used. However, CRISPR genes stay in the host cells for a long time once delivered, causing unwanted gene editing and thus posing a major concern for CRISPR/Cas9 based gene therapy in human health. Additionally, the constitutive expression of Cas9 gene in the host may elicit immunogenic response, making CRISPR gene therapy less practical for clinical applications.

Delivery of Cas9 protein along with a guide RNA (Cas9-ribonulceoprotein, or Cas9-RNP) is an alternative to these challenges, as delivered Cas9 protein offers a transient way of editing genes, and provides additional advantage for spatiotemporal control of gene transcription and imaging genome dynamics Although a few strategies for Cas9 protein delivery have been reported, a highly effective delivery of the Cas9-RNP into the cell nucleus remains challenging. A common drawback of the reported methods is the endosomal entrapment of the delivered protein, resulting in the 'wasting' of all or most of the delivered proteins, thus limiting their usage for the aforementioned applications. Moreover, delivery methods including electroporation and membrane deformation are impractical for in vivo therapeutic applications.

Figure 11A:
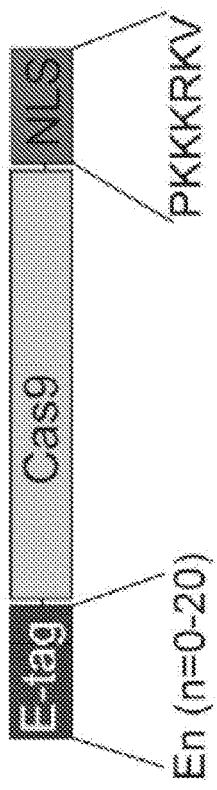
FIG. 11A illustrates a scheme showing the engineering of Cas9 to carry an N-terminus E-tag and a C-terminus nuclear localization signal (NLS), in accordance with various embodiments.
Figure 11B:
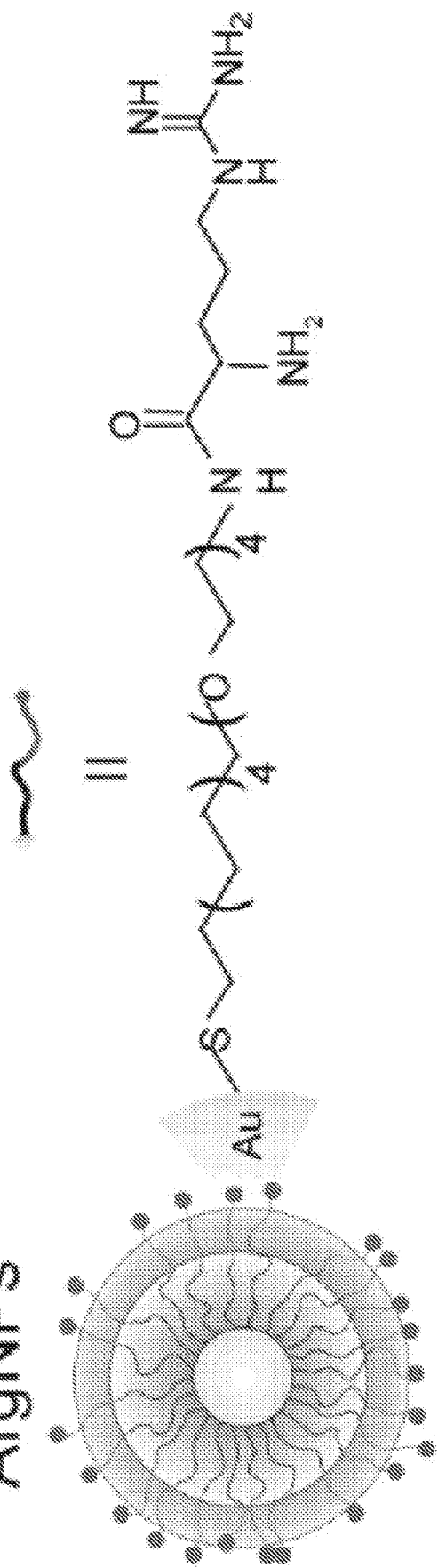
FIG. 11B illustrates a scheme showing the chemical structure of ArgNPs, in accordance with various embodiments.
Figure 11C:
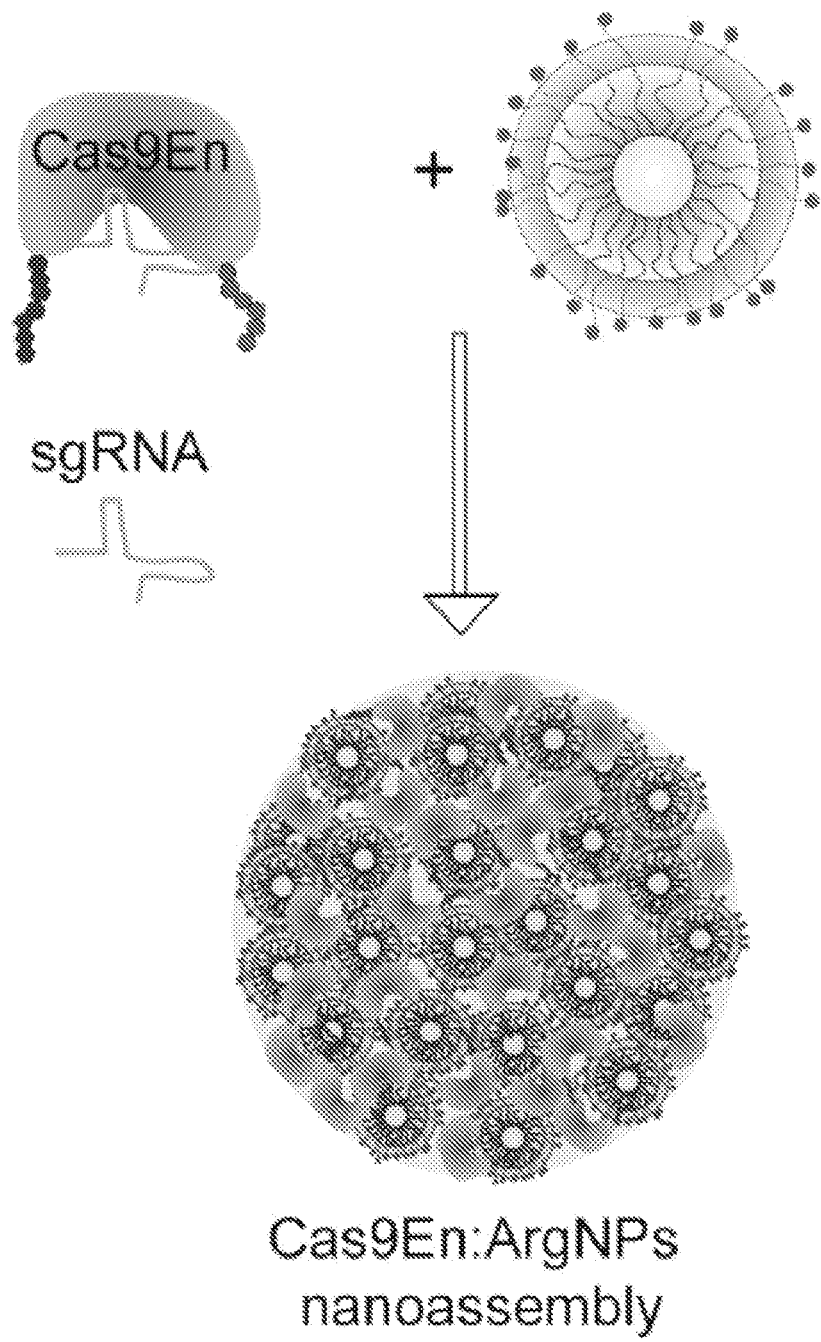
FIG. 11C illustrates a scheme showing nanoassembly formation by Cas9En-RNP and ArgNPs, in accordance with various embodiments.
Figure 11D:
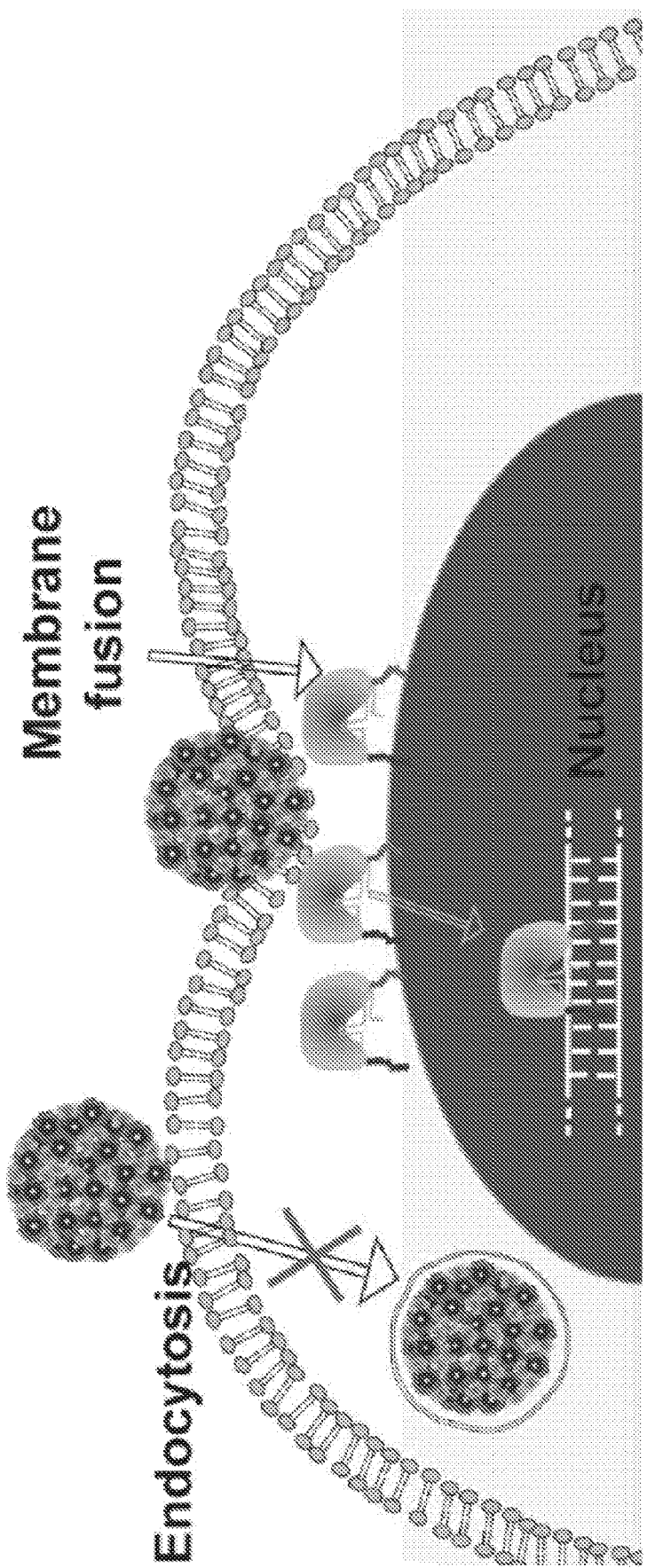
FIG. 11D illustrates a scheme showing delivery of Cas9-RNP via membrane fusion mechanism, in accordance with various embodiments.

It was envisioned that engineering of the Cas9 protein could facilitate the interaction with nanomaterial-based carriers to enhance its intracellular delivery. An approach for rational engineering of Cas9 protein was used that enabled interaction with gold nanoparticle nanocarriers, and resulted in efficient delivery of the protein directly into cells' cytoplasm/nucleus. The simultaneous engineering approach of Cas9 protein and nanoparticle was done by inserting a peptide tag comprising glutamic acids (E-tags) at the N-terminus of Streptococcus pyogenes (Sp) Cas9 protein via genetic manipulation (FIG. 11A, illustrating a scheme showing the engineering of Cas9 to carry an N-terminus E-tag and a C-terminus nuclear localization signal (NLS)), and gold nanoparticles carrying arginine-terminated ligands (ArgNP) (FIG. 11B, illustrating a scheme showing the chemical structure of ArgNPs). In addition, a nuclear localization signal (NLS) was inserted to Cas9 protein at the C-terminus for the purpose of targeting the nucleus. Thus, when the E-tagged Cas9 protein along with a sgRNA (Cas9En-RNP hereafter) was mixed with ArgNPs, they formed self-assembled nanoassemblies through carboxylate—guanidinium supramolecular recognitions (FIG. 11C, illustrating a scheme showing nanoassembly formation by Cas9En-RNP and ArgNPs). These nanoassemblies can fuse to cell membranes upon contact, releasing encapsulated Cas9-RNPs directly into the cell cytoplasm (FIG. 11D), and eventually to the nucleus through the attachment of the NLS. FIG. 11D illustrates a scheme showing delivery of Cas9 via membrane fusion mechanism. Fusion of nanoassemblies to the cell membrane facilitates direct release of the protein payload into cytoplasm, bypassing endosomes.

Cas9 protein carries high positive surface-charge that makes it unlikely to interact with carrier nanomaterials, and thus requiring appropriate engineering. A series of Cas9 proteins were engineered having a variable E-tag (En) length, where n=0, 5, 10, 15, and 20, to overcome the high positive charge of native Cas9 protein. Notably, a Cas9 protein with no modification (Cas9E0) possesses a net 24 positive charges, however, insertion of the E-tag provided a patch of local negative charges that enabled controlling the interaction with positively charged ArgNPs.

Having engineered and purified Cas9En proteins, fabricating self-assemblies between Cas9En-RNP and ArgNPs was focused on. Among these, Cas9E15 and Cas9E20 were found to be optimum for assembly formation and delivery applications.

Figure 12A:
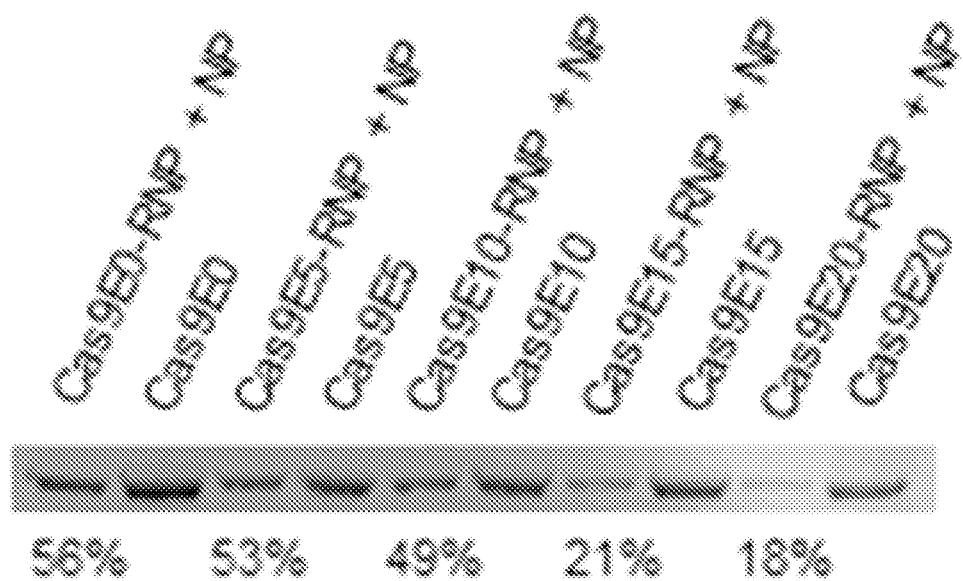
FIG. 12A illustrates sodium dodecyl sulfate polyacrylamide gel electrophoresis (SDS-PAGE) showing the unbound Cas9En proteins band and their intensities (in percentage) when mixed with ArgNPs, in accordance with various embodiments.
Figure 12B:
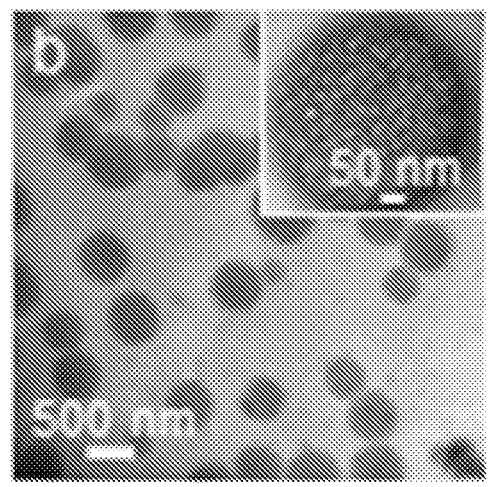
FIG. 12B illustrate TEM images showing that Cas9E15/E20-RNP formed well-defined nanoassemblies with ArgNPs, in accordance with various embodiments.

Desired self-assemblies were fabricated by mixing Cas9En-RNP and ArgNPs at various molar ratio in physiological buffer (1×PBS, pH 7.4) or in cell culture media. Following this step, the assemblies were characterized after incubating the mixture at room temperature for 10 min. Transmission electron microscopic (TEM) results suggested the formation of nanoassemblies between ArgNP and Cas9E15/E20-RNP as shown in FIG. 12B. FIG. 12B illustrate TEM images showing that Cas9E15/E20-RNP formed well defined nanoassemblies with ArgNPs. The diameter of these nanoassemblies were ~450 nm compared to individual ArgNPs (2 nm) and Cas9En (9 nm), indicating the incorporation of a large number of nanoparticles and proteins into the self-assembled structures. Interestingly, high resolution TEM images indicated the dense packing of granular proteins into the nanoassemblies (FIG. 12B inset). The optimal molar ratio for assembly formation was determined to be 1:2 (Cas9En-RNP:ArgNP), as uniform nanoassemblies were observed by TEM at this ratio (FIG. 12B). Additionally, no free ArgNPs were observed on the TEM grid at this optimized ratio, indicating complete incorporation of nanoparticles into the assemblies.

The preferential assembly formation by Cas9 containing a longer length of E-tag (E15 and E20) over the shorter ones (E0, E5, and E10) can be rationalized by the stronger binding of the former with ArgNPs. Cas9En-RNP were mixed with ArgNPs at aforementioned conditions to evaluate the binding efficiencies of these Cas9En-RNP with the nanoparticles and allow the assemblies to precipitate at room temperature. Following this, the supernatants were collected that contained unbound Cas9En. Sodium dodecyl sulfate polyacrylamide gel electrophoresis (SDS-PAGE) was used to quantify the amount of unbound proteins in these samples. FIG. 12A illustrates SDS-PAGE showing the unbound Cas9En proteins band and their intensities (in percentage) when mixed with ArgNPs. As shown in FIG. 12A, Cas9E15 and Cas9E20 exhibited higher binding (unbound Cas9E15=21%, and Cas9E20=18%) as compared to Cas9E0 (56%), Cas9E5 (51%), and Cas9E10 (48%). Although the lower length of E-tag on Cas9 was sufficient for interaction with ArgNPs to a certain extent, this interaction resulted only in the formation of extended aggregates. These results collectively indicated that the length of E-tag, hence the multivalency, can play an important role in the self-assembly formation between engineered Cas9En-RNPs and ArgNPs.

Figure 13A:
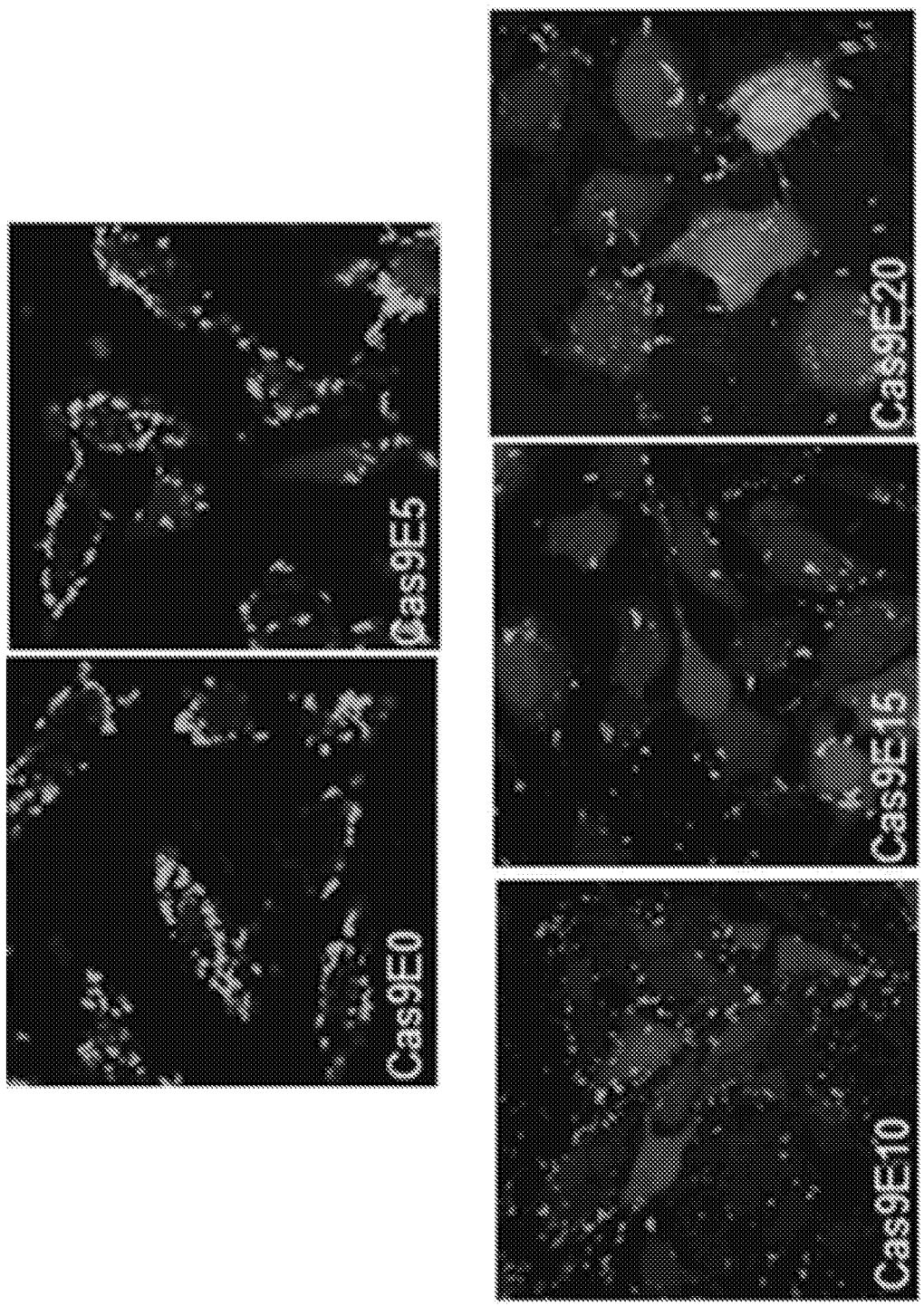
FIG. 13A illustrates photomicrographs demonstrating that cytoplasmic/nuclear delivery of FITC labelled Cas9En increased as the length of E-tag increased, in accordance with various embodiments.
Figure 13B:
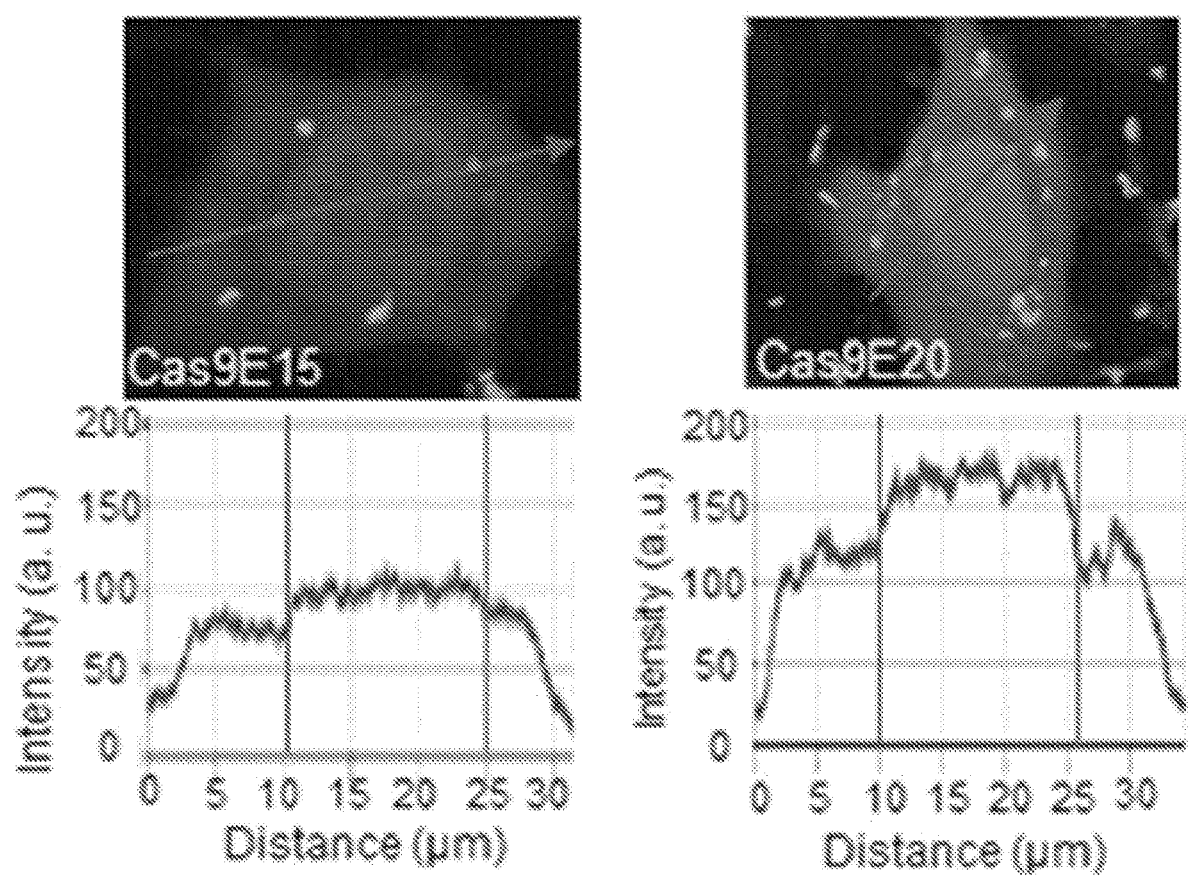
FIG. 13B illustrates the distribution of delivered Cas9En protein inside a cell, in accordance with various embodiments.

The protein delivery capability of these nanoassemblies was next investigated. To this end, Cas9En:ArgNPs assemblies were fabricated and incubated with HeLa cells in cultured media. Cas9En were labelled with fluorescein isothiocyanate (FITC) to monitor the cellular uptake efficiency. Delivery efficiency was evaluated after 3 h of incubation using confocal laser scanning microscopy (CLSM). Cytoplasmic delivery efficiency of Cas9En gradually increased as the E-tag length increased from E0 to E20, achieving maximum for Cas9E20. FIG. 13A illustrates photomicrographs demonstrating that cytoplasmic/nuclear delivery of FITC labelled Cas9En increased as the length of E-tag increased, reaching maximum at E20. Delivered Cas9En readily dispersed into cytoplasm, and reached the cell-nucleus, which is desired for efficient gene editing (FIG. 13B). FIG. 13B illustrates the distribution of delivered Cas9En protein inside a cell, showing preferential accumulation of the protein in the cytoplasm and nucleus. In contrast, poor cytoplasmic delivery of Cas9E0, Cas9E5, and Cas9E10 can be attributed to their inability to form well-defined nanoassemblies with ArgNPs. Interestingly, Cas9En with a shorter E-tag (E0 and E5) was found to bind the cell membrane, presumably due to the presence of unbound positively charged Cas9 protein in the assembly solution, which alone is capable of binding to the cell membrane.

Figure 14:
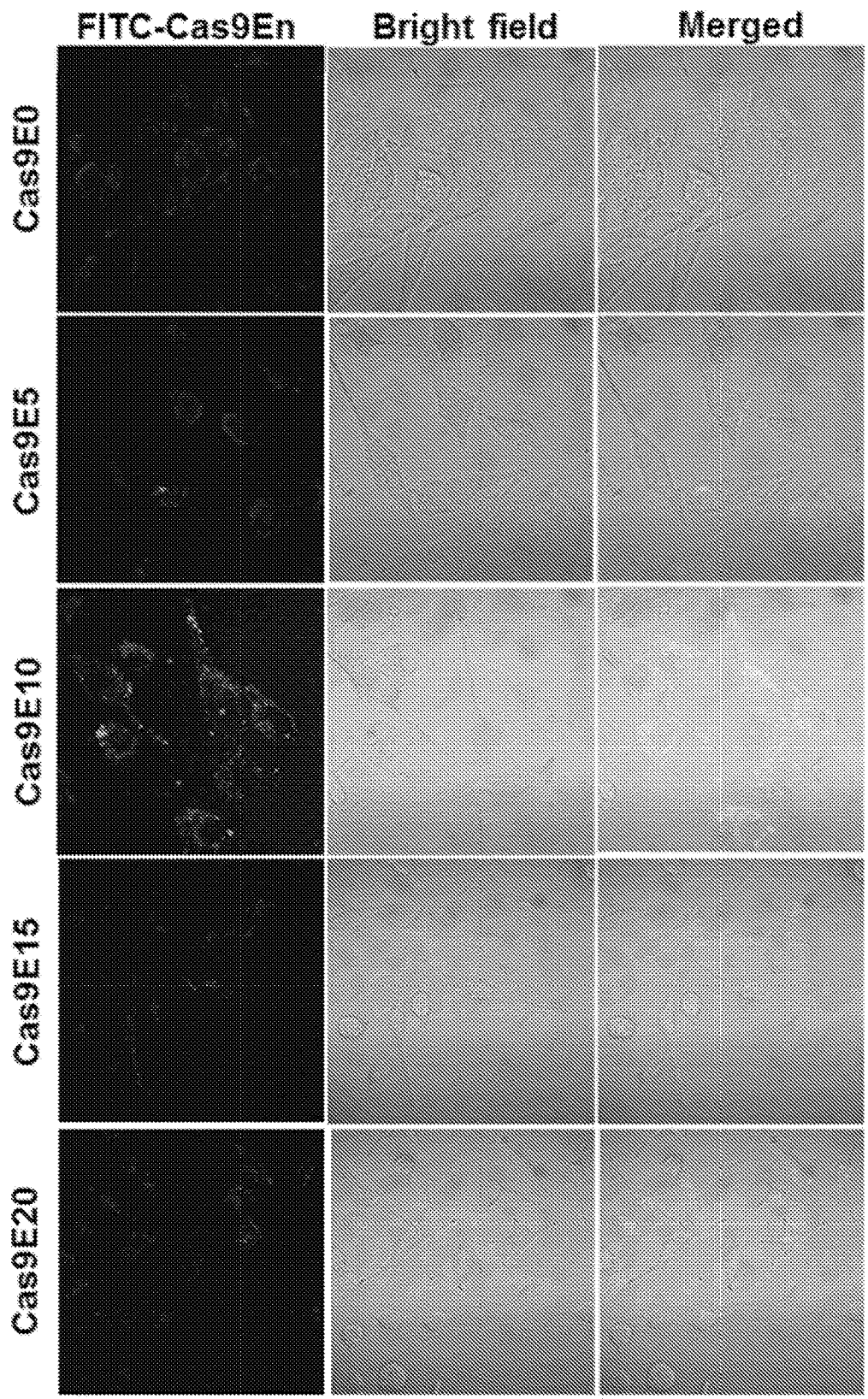
FIG. 14 illustrates confocal microscopy images showing Cas9E20 proteins, either attached to the cell membrane or trapped in the endosomes, after 3 h of incubation, in accordance with various embodiments.

Furthermore, all the Cas9En without ArgNPs, readily bound to the cell membrane (FIG. 14), demonstrating the importance of co-engineering of the protein and ArgNPs for efficient Cas9 delivery. FIG. 14 illustrates confocal microscopy images showing Cas9En proteins, either attached to the cell membrane or trapped in the endosomes, after 3 h of incubation. The images show that Cas9En protein alone does not get delivered into cell's cytoplasm/nucleus.

Figure 15:
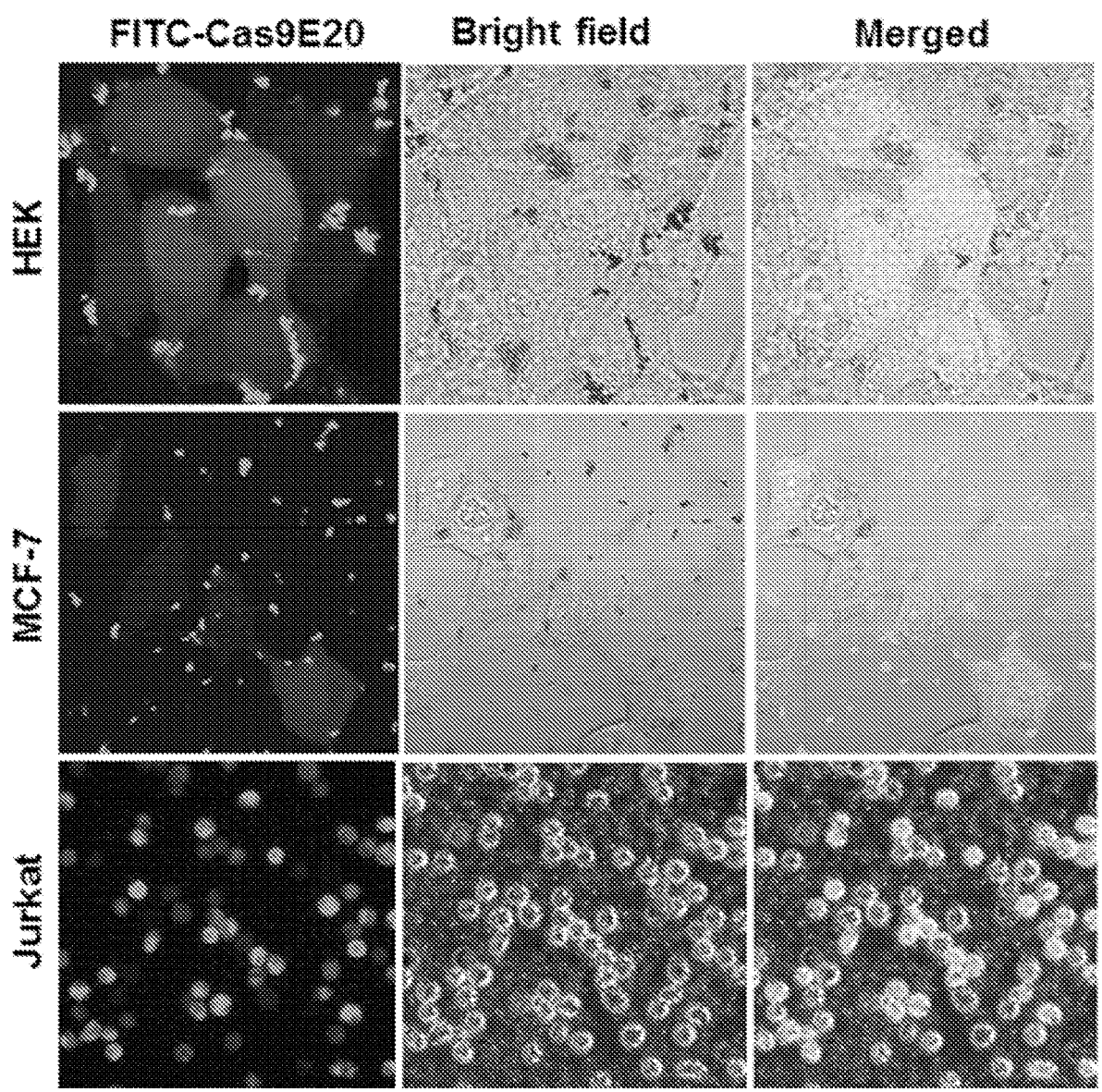
FIG. 15 illustrates confocal microscopy images showing delivered FITC-Cas9E20 after 3 h of incubation in human embryonic kidney cells (HEK), tumorous mammary epithelial cells (MCF-7), and T-lymphocytes (Jurkat), in accordance with various embodiments.

After demonstrating successful intracellular delivery of engineered Cas9-RNP into HeLa cells, its broad applicability was next investigated in different cell lines. Three human-derived cell lines were chosen: mammary epithelial cells (MCF-7), human embryonic kidney cells (HEK), and mesenchymal T-lymphocyte cells (Jurkat). Delivered Cas9E20 effectively diffused into the cell cytoplasm and nucleus in these cells (FIG. 15), similar to in HeLa cells, demonstrating the applicability of the method in various cell lines. FIG. 15 illustrates confocal microscopy images showing delivered FITC-Cas9E20 after 3 h of incubation in human embryonic kidney cells (HEK), tumorous mammary epithelial cells (MCF-7), and T-lymphocytes (Jurkat).

Figure 16:
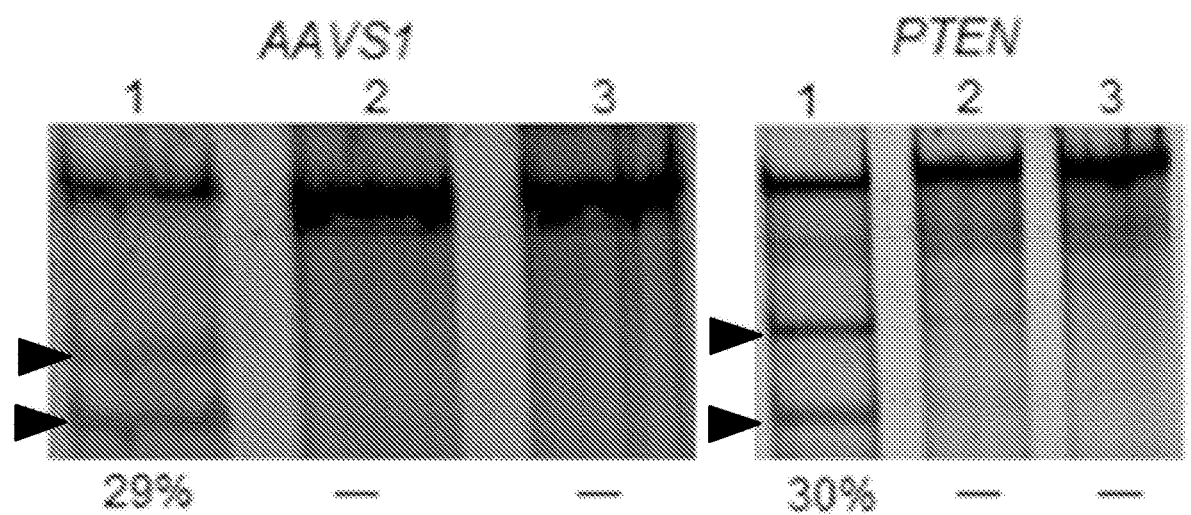
FIG. 16 illustrates an insertion and deletion (indel) assay with lane 1 showing Cas9E15-RNP:ArgNPs, lane 2 showing Cas9E15-RNP, and lane 3 showing HeLa cells, in accordance with various embodiments.

Having efficiently delivered engineered Cas9En-RNP into cells, the gene editing capability was evaluated. To this end, Cas9E15-RNP were assembled with ArgNPs targeting human AAVS1 gene and these nanoassemblies were delivered into the HeLa cells. In these experiments, the nanoassemblies were incubated with the cells for 3 h. Genome editing efficiency was evaluated after 48 h using indel (insertion and deletion) analysis. FIG. 16 illustrates an insertion and deletion (indel) assay demonstrating that delivery of Cas9E15-RNP to target AAVS1 and PTEN gene in HeLa cells resulted efficient gene editing, with lane 1 showing Cas9E15-RNP:ArgNPs, lane 2 showing Cas9E15-RNP, and lane 3 showing HeLa cells, with indel efficiency given in percentage. As evident from FIG. 16, targeting AAVS1 gene resulted up to 29% of indel efficiency. As expected, delivering Cas9E15-RNP alone did not result in gene editing, so as the untreated controls. To validate the usability of the method for any gene, the human PTEN gene was further targeted with an appropriate sgRNA. Likewise, targeting PTEN gene resulted up to 30% of indel efficiency. These results collectively showed the efficient genome editing capability of the methodology.

In summary, an engineering approach is presented to drastically enhance the cytoplasmic/nuclear delivery of Cas9-RNPs, with gene editing performed as evidence of application. The method can be easily adaptable to any newer versions of Cas9 proteins with improved specificities and altered PAM recognition. Apart from using in gene editing for clinical applications, the strategy can greatly facilitate research in many other areas of rapidly growing field of genome engineering including spatiotemporal control of gene transcription and imaging chromatin dynamics The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a nanoparticle-protein complex comprising:

a nanoparticle comprising an amine-containing ligand; and a protein comprising a carboxylic acid-containing tag.

Embodiment 2 provides the nanoparticle-protein complex of Embodiment 1, wherein the nanoparticle-protein complex has a largest dimension of about 50 nm to about 999 nm.

Embodiment 3 provides the nanoparticle-protein complex of any one of Embodiments 1-2, wherein the nanoparticle-protein complex has a largest dimension of about 150 nm to about 250 nm.

Embodiment 4 provides the nanoparticle-protein complex of any one of Embodiments 1-3, wherein the nanoparticle comprising the amine-containing ligand has a largest dimension of about 1 nm to about 50 nm.

Embodiment 5 provides the nanoparticle-protein complex of any one of Embodiments 1-4, wherein the nanoparticle comprising the amine-containing ligand has a largest dimension of about 5 nm to about 15 nm.

Embodiment 6 provides the nanoparticle-protein complex of any one of Embodiments 1-5, wherein the nanoparticle comprising the amine-containing ligand has about 1 to about 10,000 of the amine-containing ligands.

Embodiment 7 provides the nanoparticle-protein complex of any one of Embodiments 1-6, wherein the nanoparticle comprising the amine-containing ligand has about 1 to about 1,000 of the amine-containing ligands.

Embodiment 8 provides the nanoparticle-protein complex of any one of Embodiments 1-7, wherein the nanoparticle-protein complex has about 1 to about 10,000 of the nanoparticles.

Embodiment 9 provides the nanoparticle-protein complex of any one of Embodiments 1-8, wherein the nanoparticle-protein complex has about 1 to about 1,000 of the nanoparticles.

Embodiment 10 provides the nanoparticle-protein complex of any one of Embodiments 1-9, wherein the nanoparticle-protein complex has about 1 to about 10,000 molecules of the protein.

Embodiment 11 provides the nanoparticle-protein complex of any one of Embodiments 1-10, wherein the nanoparticle is a quantum dot or a nanoparticle comprising at least one of gold, iron oxide, cobalt ferrite, and silica.

Embodiment 12 provides the nanoparticle-protein complex of any one of Embodiments 1-11, wherein the amine-containing ligand is a guanidine-containing ligand.

Embodiment 13 provides the nanoparticle-protein complex of any one of Embodiments 1-12, wherein the amine-containing ligand is an arginine-containing ligand.

Embodiment 14 provides the nanoparticle-protein complex of any one of Embodiments 1-13, wherein the amine-containing ligand is an arginine-terminated ligand.

Embodiment 15 provides the nanoparticle-protein complex of any one of Embodiments 1-14, wherein the amine-containing ligand is terminated with an amine-substituted or amine-containing ($C_0$-$C_{20}$)hydrocarbyl group that is otherwise substituted or unsubstituted.

Embodiment 16 provides the nanoparticle-protein complex of Embodiment 15, wherein the amine-substituted or amine-containing ($C_0$-$C_{20}$)hydrocarbyl group is tethered to the nanoparticle via a bond or via a linker that comprises at least one of a substituted or unsubstituted $(C_1$-$C_{30})$hydrocarbylene interrupted or terminated with 0, 1, 2, or 3 groups independently chosen from —O—, —S—, and substituted or unsubstituted —NH—, and a poly(substituted or unsubstituted $(C_2$-$C_{10})$hydrocarbyloxy).

Embodiment 17 provides the nanoparticle-protein complex of any one of Embodiments 15-16, wherein the amine-substituted or amine-containing $(C_0$-$C_{20})$hydrocarbyl group is tethered to the nanoparticle via a bond or via a linker that comprises at least one of a $(C_1$-$C_{20})$alkylene and a poly$((C_2$-$C_3)$alkoxy), wherein the linker is bound to the nanoparticle via an —S—.

Embodiment 18 provides the nanoparticle-protein complex of any one of Embodiments 1-17, wherein the amine-containing ligand has the structure:

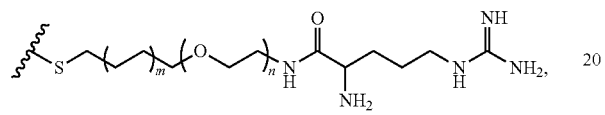

or a salt thereof, wherein m is 0 to 1,000 and n is 0 to 1,000.

Embodiment 19 provides the nanoparticle-protein complex of any one of Embodiments 1-18, wherein the amine-containing ligand has the structure:

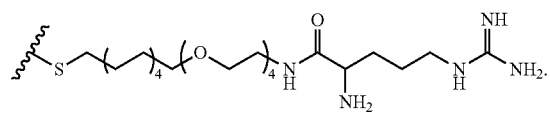

Embodiment 20 provides the nanoparticle-protein complex of any one of Embodiments 1-19, wherein the protein is chosen from GFP, Granzyme A, mCherry, Cre recombinase, Cas9, Histone 2A, and combinations thereof.

Embodiment 21 provides the nanoparticle-protein complex of any one of Embodiments 1-20, wherein in solution the protein has a largest dimension of about 0.5 nm to about 50 nm.

Embodiment 22 provides the nanoparticle-protein complex of any one of Embodiments 1-21, wherein in solution the protein has a largest dimension of about 1 nm to about 30 nm.

Embodiment 23 provides the nanoparticle-protein complex of any one of Embodiments 1-22, wherein the carboxylic acid-containing tag is on at least one of a C-terminus and an N-terminus of the protein.

Embodiment 24 provides the nanoparticle-protein complex of any one of Embodiments 1-23, wherein the carboxylic acid-containing tag is a polycarboxylic acid tag.

Embodiment 25 provides the nanoparticle-protein complex of any one of Embodiments 1-24, wherein the carboxylic acid-containing tag is a poly(amino acid) tag.

Embodiment 26 provides the nanoparticle-protein complex of any one of Embodiments 1-25, wherein the carboxylic acid-containing tag comprises a glutamic acid tag.

Embodiment 27 provides the nanoparticle-protein complex of any one of Embodiments 1-26, wherein the carboxylic acid-containing tag comprises a poly(glutamic acid) tag.

Embodiment 28 provides the nanoparticle-protein complex of any one of Embodiments 1-27, wherein the carboxylic acid-containing tag has the structure:

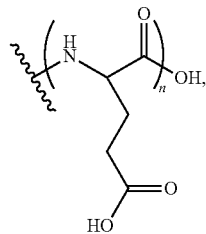

or a salt thereof, or,

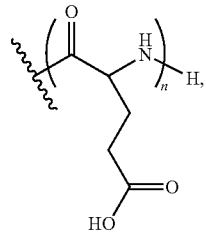

or a salt thereof,
wherein n is about 1 to about 10,000.

Embodiment 29 provides the nanoparticle-protein complex of Embodiment 28, wherein n is about 5 to about 20.

Embodiment 30 provides the nanoparticle-protein complex of any one of Embodiments 1-29, further comprising a nucleic acid material.

Embodiment 31 provides the nanoparticle-protein complex of Embodiment 30, wherein the nucleic acid material is at least one of DNA and RNA.

Embodiment 32 provides the nanoparticle-protein complex of any one of Embodiments 30-31, wherein the nucleic acid material is at least one of mRNA (messenger RNA), rRNA (ribosomal RNA), 7SL RNA or SRP RNA (signal recognition particle RNA), tRNA (transfer RNA), tmRNA (transfer-messenger RNA), snRNA (small nuclear RNA), snoRNA (small nucleolar RNA), SmY (SmY RNA), scaRNA (small Cajal body-specific RNA), gRNA (guide RNA), catalytic RNA, RNase P (ribonuclease P), RNase MRP (ribonuclease MRP), oligonucleotide RNA, Y RNA, TERC (telomerase RNA component), SL RNA (spliced leader RNA), aRNA or asRNA (antisense RNA), cis-NAT (cis-natural antisense transcript), crRNA (CRISPR RNA), lncRNA (long noncoding RNA), miRNA (microRNA), piRNA (piwi-interacting RNA), siRNA (small interfering RNA), tasiRNA (trans-acting siRNA), rasiRNA (repeat associated siRNA), and 7SK (7SK RNA).

Embodiment 33 provides the nanoparticle-protein complex of any one of Embodiments 30-32, wherein the nucleic acid material is gRNA (guide RNA).

Embodiment 34 provides the nanoparticle-protein complex of any one of Embodiments 30-33, wherein the nanoparticle-protein complex has about 1 to about 10,000 molecules of the nucleic acid material.

Embodiment 35 provides the nanoparticle-protein complex of any one of Embodiments 30-34, wherein the nucleic acid material and the protein form a complex.

Embodiment 36 provides the nanoparticle-protein complex of Embodiment 35, wherein the complex is a 1:1 molar complex of the nucleic acid material and the protein.

Embodiment 37 provides the nanoparticle-protein complex of any one of Embodiments 1-36, wherein the protein further comprises an organelle-localization signal.

Embodiment 38 provides the nanoparticle-protein complex of Embodiment 37, wherein the organelle-localization signal is located at the C-terminus or the N-terminus of the protein.

Embodiment 39 provides the nanoparticle-protein complex of any one of Embodiments 37-38, wherein the organelle-localization signal is a simian virus SV30 nuclear localization signal.

Embodiment 40 provides the nanoparticle-protein complex of any one of Embodiments 1-39, further comprising an antibody.

Embodiment 41 provides the nanoparticle-protein complex of Embodiment 40, wherein the antibody comprises a carboxylic acid-containing tag.

Embodiment 42 provides a method of using the nanoparticle-protein complex of any one of Embodiments 1-41 to deliver the protein to a cell.

Embodiment 43 provides the method of Embodiment 42, comprising contacting the nanoparticle-protein complex with one or more cells.

Embodiment 44 provides the method of Embodiment 43, comprising allowing the nanoparticle-protein complex to release the protein within the cell.

Embodiment 45 provides the method of any one of Embodiments 43-44, comprising allowing the nanoparticle-protein complex to release the protein within the cell cytoplasm of the cell.

Embodiment 46 provides a method of using the nanoparticle-protein complex of any one of Embodiments 30-45 to deliver the protein and the nucleic acid material to a cell.

Embodiment 47 provides the method of Embodiment 46, comprising contacting the nanoparticle-protein complex with one or more cells.

Embodiment 48 provides the method of Embodiment 47, comprising allowing the nanoparticle-protein complex to release the protein and the nucleic acid material within the cell.

Embodiment 49 provides the method of any one of Embodiments 47-48, comprising allowing the nanoparticle-protein complex to release the protein and the nucleic acid material within the cell cytoplasm of the cell.

Embodiment 50 provides a nanoparticle-protein complex comprising:

a gold nanoparticle comprising an amine-containing ligand having the structure:

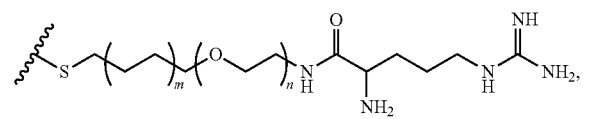

or a salt thereof, wherein m is 0 to 1,000 and n is 0 to 1,000; and a protein comprising a carboxylic acid-containing tag having the structure:

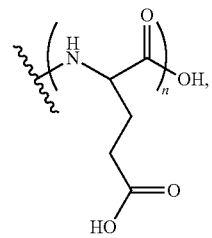

or a salt thereof,
or,

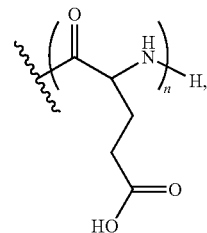

or a salt thereof,
wherein n is about 1 to about 10,000, wherein the protein is chosen from GFP, Granzyme A, mCherry, Cre recombinase, Cas9, Histone 2A, and combinations thereof;
wherein the nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, and the nanoparticle-protein complex has about 1 to about 10,000 molecules of the protein.

Embodiment 51 provides a nanoparticle-protein complex comprising:

a gold nanoparticle comprising an amine-containing ligand having the structure:

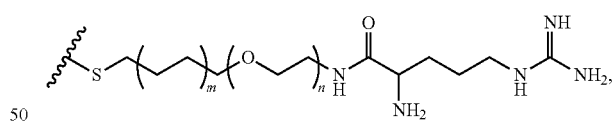

or a salt thereof, wherein m is 0 to 1,000 and n is 0 to 1,000;
a protein comprising a carboxylic acid-containing tag having the structure:

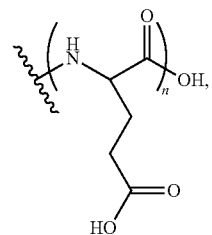

or a salt thereof,
or,

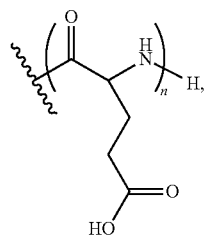

or a salt thereof,
wherein n is about 1 to about 10,000, wherein the protein is chosen from GFP, Granzyme A, mCherry, Cre recombinase, Cas9, Histone 2A, and combinations thereof; and a nucleic acid material that is gRNA;

wherein the nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, the nanoparticle-protein complex has about 1 to about 10,000 molecules of the protein, and the nanoparticle-protein complex has about 1 to about 10,000 molecules of the nucleic acid material.

Embodiment 52 provides a method of intracellular protein delivery, comprising:

contacting a nanoparticle-protein complex with a cell, the nanoparticle-protein complex comprising a nanoparticle comprising an amine-containing ligand; and a protein comprising a carboxylic acid-containing tag; and delivering the protein into the cell from the nanoparticle-protein complex.

Embodiment 53 provides a method of intracellular protein and nucleic acid material delivery, comprising:

contacting a nanoparticle-protein complex with a cell, the nanoparticle-protein complex comprising a nanoparticle comprising an amine-containing ligand;

a protein comprising a carboxylic acid-containing tag; and a nucleic acid material; and delivering the protein and the nucleic acid material into the cell from the nanoparticle-protein complex.

Embodiment 54 provides the method of Embodiment 53, wherein the nanoparticle-protein complex further comprises an antibody comprising a carboxylic acid-containing tag, wherein the method further comprises targeting specific cells for protein delivery with the nanoparticle-protein complex.

Embodiment 55 provides the method of any one of Embodiments 53-54, wherein the protein comprises an organelle-localization signal, wherein the method further comprises targeting specific cell organelles for protein delivery with the nanoparticle-protein complex.

Embodiment 56 provides a method of intracellular protein delivery, comprising:

contacting a nanoparticle-protein complex with a cell, the nanoparticle-protein complex comprising a nanoparticle comprising an amine-containing ligand having the structure:

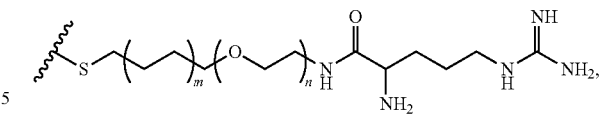

or a salt thereof, wherein m is 0 to 1,000 and n is 0 to 1,000; and a protein comprising a carboxylic acid-containing tag having the structure:

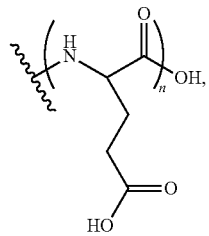

or a salt thereof,
or,

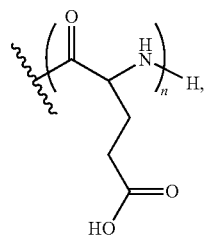

or a salt thereof,
wherein n is about 1 to about 10,000, wherein the protein is chosen from GFP, Granzyme A, mCherry, Cre recombinase, Cas9, Histone 2A, and combinations thereof;

wherein the nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, and the nanoparticle-protein complex has about 1 to about 10,000 molecules of the protein; and delivering the protein into the cell from the nanoparticle-protein complex.

Embodiment 57 provides a method of intracellular protein and nucleic acid material delivery, comprising:

contacting a nanoparticle-protein complex with a cell, the nanoparticle-protein complex comprising a gold nanoparticle comprising an amine-containing ligand having the structure:

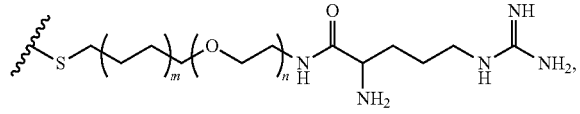

or a salt thereof, wherein m is 0 to 1,000 and n is 0 to 1,000; and a protein comprising a carboxylic acid-containing tag having the structure:

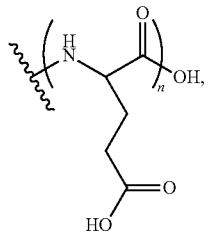

or a salt thereof, or,

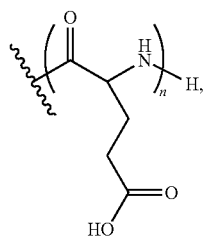

or a salt thereof, wherein n is about 1 to about 10,000, wherein the protein is chosen from GFP, Granzyme A, mCherry, Cre recombinase, Cas9, Histone 2A, and combinations thereof; and a nucleic acid material that is gRNA;

wherein the nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, the nanoparticle-protein complex has about 1 to about 10,000 molecules of the protein, and the nanoparticle-protein complex has about 1 to about 10,000 molecules of the gRNA; and delivering the protein and the nucleic acid material into the cell from the nanoparticle-protein complex.

Embodiment 58 provides a method of forming a nanoparticle-protein complex, the method comprising:

combining a nanoparticle comprising an amine-containing ligand with a protein comprising a carboxylic acid-containing tag to form a self-assembled nanoparticle-protein complex.

Embodiment 59 provides a method of forming a nanoparticle-protein complex, the method comprising:

combining a nanoparticle comprising an amine-containing ligand with a protein comprising a carboxylic acid-containing tag and a nucleic acid material to form a self-assembled nanoparticle-protein complex that comprises the nucleic acid material.

Embodiment 60 provides a method of forming a nanoparticle-protein complex, the method comprising:

combining a gold nanoparticle comprising an amine-containing ligand having the structure:

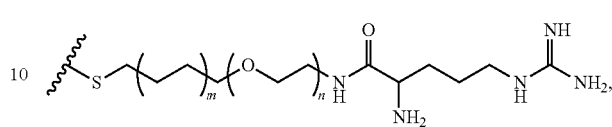

or a salt thereof, wherein m is 0 to 1,000 and n is 0 to 1,000, wherein the gold nanoparticle has a largest dimension of about 1 nm to about 50 nm and the gold nanoparticle has about 1 to about 10,000 of the amine-containing ligands, with a protein comprising a carboxylic acid-containing tag having the structure:

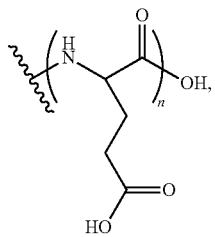

or a salt thereof, or,

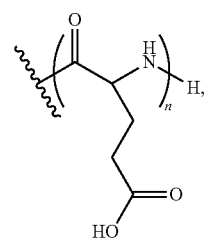

or a salt thereof, wherein n is about 1 to about 10,000, wherein the protein is chosen from GFP, Granzyme A, mCherry, Cre recombinase, Cas9, Histone 2A, and combinations thereof, wherein in solution the protein has a largest dimension of about 0.5 nm to about 50 nm;

to form a self-assembled nanoparticle-protein complex, wherein the nanoparticle-protein complex has a largest dimension of about 50 to about 999 nm, the nanoparticle-protein complex has about 1 to about 10,000 of the gold nanoparticles, and the nanoparticle-protein complex has about 1 to about 10,000 molecules of the protein.

Embodiment 61 provides a method of forming a nanoparticle-protein complex, the method comprising:

combining a gold nanoparticle comprising an amine-containing ligand having the structure:

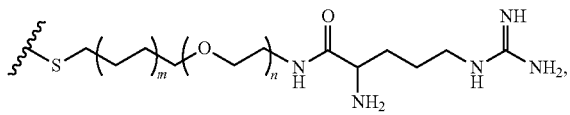

or a salt thereof, wherein m is 0 to 1,000 and n is 0 to 1,000, wherein the gold nanoparticle has a largest dimension of about 1 nm to about 50 nm and the gold nanoparticle has about 1 to about 10,000 of the amine-containing ligands, with
   a complex comprising
      a protein comprising a carboxylic acid-containing tag having the structure:

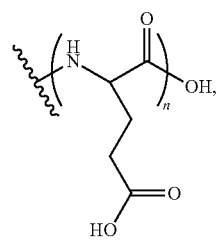

or a salt thereof,
or,

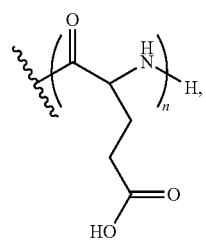

or a salt thereof,
      wherein n is about 1 to about 10,000, wherein the protein is chosen from GFP, Granzyme A, mCherry, Cre recombinase, Cas9, Histone 2A, and combinations thereof, wherein in solution the protein has a largest dimension of about 0.5 nm to about 50 nm, and
      a nucleic acid material that is gRNA;
   to form a self-assembled nanoparticle-protein complex that comprises the nucleic acid material, wherein the nanoparticle-protein complex has a largest dimension of about 50 to about 999 nm, the nanoparticle-protein complex has about 1 to about 10,000 of the gold nanoparticles, the nanoparticle-protein complex has about 1 to about 10,000 molecules of the protein, and the nanoparticle-protein complex has about 1 to about 10,000 molecules of the gRNA.

Embodiment 61 provides the nanoparticle-protein complex or method of any one or any combination of Embodiments 1-60 optionally configured such that all elements or options recited are available to use or select from.

What is claimed is:

1. A nanoparticle-protein complex comprising:
a nanoparticle comprising an amine-containing ligand;
a protein comprising a carboxylic acid-containing tag, wherein the amine-containing ligand and carboxylic acid-containing tag are joined by an electrostatic interaction to form the nanoparticle-protein complex;
a nucleic acid material, having a largest dimension in a range of from about 0.5 nm to about 1000 nm and a molar ratio of protein to nucleic acid is at least about 1:1, wherein
the nanoparticle-protein complex has a largest dimension of about 50 nm to about 999 nm.

2. The nanoparticle-protein complex of claim 1, wherein the nanoparticle-protein complex has about 1 to about 10,000 of the nanoparticles.

3. The nanoparticle-protein complex of claim 1, wherein the nanoparticle-protein complex has about 1 to about 10,000 molecules of the protein.

4. The nanoparticle-protein complex of claim 1, wherein the nanoparticle comprises at least one of gold, iron oxide, cobalt ferrite, and silica.

5. The nanoparticle-protein complex of claim 1, wherein the amine-containing ligand is a guanidine-containing ligand or an arginine-containing ligand.

6. The nanoparticle-protein complex of claim 1, wherein the amine-containing ligand has the structure:

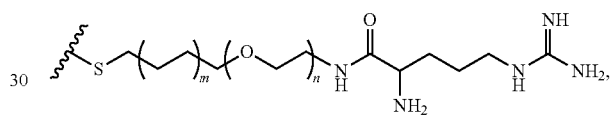

or a salt thereof, wherein m is 0 to 1,000 and n is 0 to 1,000.

7. The nanoparticle-protein complex of claim 1, wherein the amine-containing ligand has the structure:

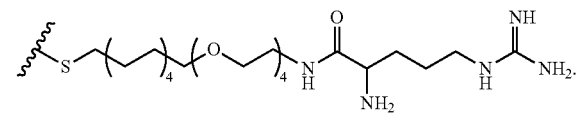

8. The nanoparticle-protein complex of claim 1, wherein the protein is chosen from GFP, Granzyme A, mCherry, Cre recombinase, Cas9, Histone 2A, and combinations thereof.

9. The nanoparticle-protein complex of claim 1, wherein the carboxylic acid -containing tag comprises a glutamic acid tag or a poly(glutamic acid) tag.

10. The nanoparticle-protein complex of claim 1, wherein the carboxylic acid -containing tag has the structure:

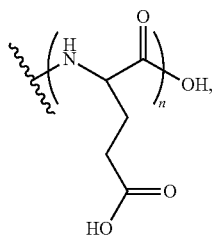

or a salt thereof, or,

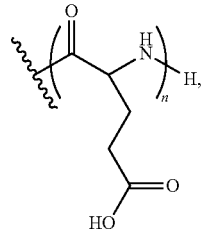

or a salt thereof,
wherein n is about 1 to about 10,000.

11. The nanoparticle-protein complex of claim 10, wherein n is about 5 to about 20.

12. The nanoparticle-protein complex of claim 1, wherein the nucleic acid material comprises at least one of mRNA (messenger RNA), rRNA (ribosomal RNA), 7SL RNA or SRP RNA (signal recognition particle RNA), tRNA (transfer RNA), tmRNA (transfer-messenger RNA), snRNA (small nuclear RNA), snoRNA (small nucleolar RNA), SmY (SmY RNA), scaRNA (small Cajal body-specific RNA), gRNA (guide RNA), catalytic RNA, RNase P (ribonuclease P), RNase MRP (ribonuclease MRP), oligonucleotide RNA, Y RNA, TERC (telomerase RNA component), SL RNA (spliced leader RNA), aRNA or asRNA (antisense RNA), cis-NAT (cis-natural antisense transcript), crRNA (CRISPR RNA), lncRNA (long noncoding RNA), miRNA (micro-RNA), piRNA (piwi-interacting RNA), siRNA (small interfering RNA), tasiRNA (trans-acting siRNA), rasiRNA (repeat associated siRNA), and 7SK (7SK RNA).

13. The nanoparticle-protein complex of claim 1, wherein the nucleic acid material is gRNA (guide RNA).

14. The nanoparticle-protein complex of claim 1, wherein the protein further comprises an organelle-localization signal.

15. The nanoparticle-protein complex of claim 1, further comprising an antibody comprising a carboxylic acid-containing tag.

16. A method of using the nanoparticle-protein complex of claim 1 to deliver the protein to a cell, comprising contacting the nanoparticle-protein complex with one or more cells.

17. A method of forming the nanoparticle-protein complex of claim 1, the method comprising:
combining the nanoparticle comprising an amine-containing ligand with the protein comprising a carboxylic acid-containing tag to form a self-assembled nanoparticle-protein complex that is the nanoparticle-protein complex of claim 1.

18. A nanoparticle-protein complex comprising:
a gold nanoparticle comprising an amine-containing ligand having the structure:

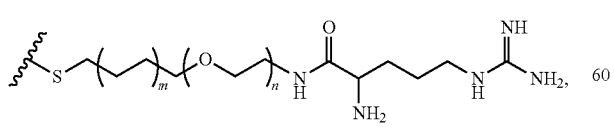

or a salt thereof, wherein m is 0 to 1,000 and n is 0 to 1,000;
a protein comprising a carboxylic acid-containing tag having the structure:

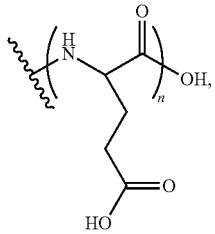

or a salt thereof,
or,

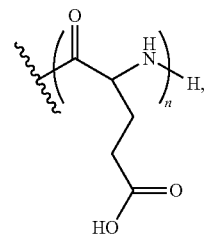

or a salt thereof,
wherein n is about 1 to about 10,000, wherein the protein is chosen from GFP, Granzyme A, mCherry, Cre recombinase, Cas9, Histone 2A, and combinations thereof; and a nucleic acid material, having a largest dimension in a range of from about 0.5 nm to about 999 nm and a molar ratio of protein to nucleic acid is at least about 1:1, wherein the nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, and the nanoparticle-protein complex has about 1 to about 10,000 molecules of the protein and the amine-containing ligand and carboxylic acid-containing tag are joined by an electrostatic interaction to form the nanoparticle-protein complex.

19. A nanoparticle-protein complex comprising:
a gold nanoparticle comprising an amine-containing ligand having the structure:

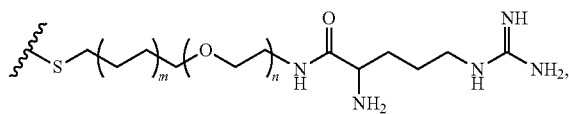

or a salt thereof, wherein m is 0 to 1,000 and n is 0 to 1,000;
a protein comprising a carboxylic acid-containing tag having the structure:

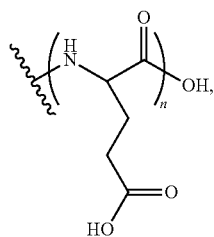

or a salt thereof,
or,

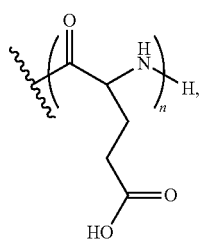

or a salt thereof, wherein n is about 1 to about 10,000, wherein the protein is chosen from GFP, Granzyme A, mCherry, Cre recombinase, Cas9, Histone 2A, and combinations thereof;

a nucleic acid material that is gRNA, having a largest dimension in a range of from about 0.5 nm to about 999 nm and a molar ratio of protein to nucleic acid is at least about 1:1;

wherein the nanoparticle-protein complex has a largest dimension of about 50 to about 999 nm, the gold nanoparticle has a largest dimension of about 1 nm to about 50 nm, in solution the protein has a largest dimension of about 0.5 nm to about 50 nm, the gold nanoparticle has about 1 to about 10,000 of the amine-containing ligands, the nanoparticle-protein complex has about 1 to about 10,000 of the gold nanoparticles, the nanoparticle-protein complex has about 1 to about 10,000 molecules of the protein, and the nanoparticle-protein complex has about 1 to about 10,000 molecules of the nucleic acid material and the amine-containing ligand and carboxylic acid -containing tag are joined by an electrostatic interaction to form the nanoparticle-protein complex.

* * * * *